US007875650B2

(12) United States Patent
Cheng et al.

(10) Patent No.: US 7,875,650 B2
(45) Date of Patent: Jan. 25, 2011

(54) COMPOUNDS AND METHODS TO INCREASE ANTI-P-GLYCOPROTEIN ACTIVITY OF BAICALEIN BY ALKYLATION ON THE A RING

(75) Inventors: Yung-chi Cheng, Woodbridge, CT (US); Yashang Lee, New Haven, CT (US); Hosup Yeo, Daegu (KR)

(73) Assignee: Yale University, New Haven, CT (US)

( * ) Notice: Subject to any disclaimer, the term of this patent is extended or adjusted under 35 U.S.C. 154(b) by 1077 days.

(21) Appl. No.: 10/586,822

(22) PCT Filed: Jan. 31, 2005

(86) PCT No.: PCT/US2005/002910

§ 371 (c)(1),
(2), (4) Date: Oct. 13, 2006

(87) PCT Pub. No.: WO2005/075449

PCT Pub. Date: Aug. 18, 2005

(65) Prior Publication Data

US 2007/0161605 A1 Jul. 12, 2007

Related U.S. Application Data

(60) Provisional application No. 60/541,443, filed on Feb. 3, 2004.

(51) Int. Cl.
*A61K 31/35* (2006.01)
(52) U.S. Cl. .................................................. 514/456
(58) Field of Classification Search ............... 514/456
See application file for complete search history.

(56) References Cited

U.S. PATENT DOCUMENTS

| 6,793,944 B2 * | 9/2004 | Sheu et al. .................. 424/725 |
| 6,806,257 B1 * | 10/2004 | Lee et al. ........................ 514/23 |
| 6,888,014 B2 * | 5/2005 | Huang et al. ................. 552/502 |
| 2008/0050426 A1 * | 2/2008 | Park et al. .................... 424/451 |

FOREIGN PATENT DOCUMENTS

| JP | 61137818 A | * | 6/1986 |
| WO | WO 9731933 A1 | * | 9/1997 |

OTHER PUBLICATIONS

Luer et al., The Annals of Pharmacotherapy, abstract, vol. 27, No. 7, pp. 912-921.*
Afifi, F.U., (2004) "Antiplatelet activity of *Varthemia iphionoides*" *Fitoterapia* 75:629-633.
Zia-Ul-Haq, M. et al., (2002) "Synthesis of 1,4-Diazepine Nucleosides" *Turk. J. Chem.* 26:807-813.
German, U. A. P-glycoprotein—a mediator of multidrug resistance in tumour cells. *Eur J Cancer* 1996, 32A, 927-944.
Gottesman, M. M.; Pastan, I. Biochemistry of multidrug resistance mediated by the multidrug transporter. *Annu Rev Biochem* 1993, 62, 385-427.
Thiebaut, F.; Tsuruo, T.; Hamada, H.; Gottesman, M. M.; Pastan, I. et al. Cellular localization of the multidrug-resistance gene product P-glycoprotein in normal human tissues. *Proc Nat/ Acad Sci USA* 1987, 84, 7735-7738.
Borst, P.; Schinkel, A. H. What have we learnt thus far from mice with disrupted P-glycoprotein genes? *Eur J Cancer* 1996, 32A, 985-990.
Luker, G. D.; Nilsson, K. R.; Covey, D. F.; Piwmica-Worms, D. Multidrug resistance (MDRI) P-glycoprotein enhances esterification of plasma membrane cholesterol. *J Biol Chem* 1999, 274, 6979-6991.
Dalton, W. S.; Grogan, T. M.; Meltzer, P. S.; Scheper, R. J.; Dude, B. G. et al. Drug-resistance in multiple myeloma and non-Hodgkin's lymphoma: detection of P- glycoprotein and potential circumvention by addition of verapamil to chemotherapy. *J Clin Oncol* 1989, 7, 415-424.
Miller, T. P.; Grogan, T. M.; Dalton, W. S.; Spier, C. M.; Scheper, R. J. et al. P-glycoprotein expression in malignant lymphoma and reversal of clinical drug resistance with chemotherapy plus high-dose verapamil. *J Clin Oncol* 1991, 9, 17-24.
Nuessler, V.; Scheulen, M. E.; Oberneder, R.; Kriegmair, M.; Goebel, K, J. et al. Phase I and pharmacokinetic study of the P-glycoprotein modulator dexniguldipine-HCL. *Eur J Med Res* 1997, 2, 55-61.
Wilson, W. H.; Jamis-Dow, C.; Bryant, G.; Balis, F. M.; Klecker, R. W. et al. Phase I and pharmacokinetic study of the multidrug resistance modulator dexverapnil with EPOCH chemotherapy. *J Clin Oncol* 1995, 13, 1985-1994.
Hyafil, F.; Vergely, C.; Du Vignaud, P.; Grand-Perret, T. In vitro and in vivo reversal of multidrug resistance by GF120918, an acridonecarboxamide derivative. *Cancer Res* 1993, 53, 4595-4602.
Boesch, D.; Gaveriaux, C.; Jachez, B.; Pourtier-Manzanedo, A.; Bollinger, P. et al. In vivo circumvention of P-glycoprotein-mediated multidrug resistance of tumor cells with SDZ PSC 833. *Cancel Res* 1991, 51, 4226-4233.

(Continued)

*Primary Examiner*—Raymond J Henley, III
(74) *Attorney, Agent, or Firm*—Henry D. Coleman; R. Neil Sudol; William J. Sapone

(57) ABSTRACT

The present invention is directed to analogs of baicalein according to formula (I): where $R^5$ is H, $(C_1-C_{12})$alkyl, $(C_2-C_{13})$acyl, or an optionally substituted phenyl or benzyl group, an acyl group, a $C_1-C_{20}$ alkyl or ether group, a phosphate, diphosphate, triphosphate or phosphodiester group; $R^6$ and $R^7$ are each independently H, $(C_1-C_{12})$alkyl, $(C_2-C_{13})$acyl, or an optionally substituted phenyl or benzyl or together form a —$OCR^1R^2O$— group wherein each of $R^1$ and $R^2$ is independently H, a $C_1-C_3$ alkyl group or an optionally substituted phenyl or benzyl group; and $R^8$ is H, OH, an O-acyl group, a $C_1$-$C_4$ alkyl or alkoxy group, F, Cl, Br or I, or a pharmaceutically acceptable salt thereof, which exhibit anti-P-glycoprotein activity and methods of enhancing the bioavailability of active compounds, especially orally administered compounds, by inhibition of P-glycoprotein 170 (P-gp 170) and/or CYP450 enzyme, especially CYP450 3A4 enzyme. Pharmaceutical compositions based upon these novel derivatives according to the present invention are also described herein.

24 Claims, 4 Drawing Sheets

OTHER PUBLICATIONS

Ramu, A.; Spanier, R.; Rahamimoff, H.; Fuks, Z. Restoration of doxorubicin responsiveness in doxorubicin-resistant P388 murine leukaemia cells. *Br J Cancer* 1984, 50, 501-507.

Middleton, E., Jr.; Kandaswami, C.; Theoharides, T. C. The effects of plant flavonoids on mammalian cells: implications for inflammation, heart disease, and cancer. *Pharmacol Rev* 2000, 52, 673-751.

Bailey, D. G.; Malcolm, J.; Arnold, 0.; Spence, J. D. Grapefruit juice-drug interactions. *Br J Clin Pharmacol* 1998, 46, 101-110.

Ducharme, M. P.; Warbasse, L. H.; Edwards, D. J. Disposition of intravenous and oral cyclosporine after administration with grapefruit juice. *Clin Pharmacol The?* 1995, 57, 485-491.

De Vincenzo, R.; Scambia, G.; Benedetti Panici, P.; Ranelletti, F. 0.; Bonanno, G. et al. Effect of synthetic and naturally occurring chalcones on ovairan cancer cell growth: structure-activity relationships. *Anticancer Drug Des* 1995, 10, 481-490.

Murakami, S.; Muramatsu, M.; Tomisawa, K. Inhibition of gastric H+, K(+)-ATPase by flavonoids: a structure-activity study. *J Enzyme brhib* 1999, 14, 151-166.

Akiyama, T.; Ishida, J.; Nakagawa, S.; Ogawara, H.; Watanabe, S. et al. Genistein, a specific inhibitor of tyrosine-specific protein kinases. *J Biol Chem* 1987, 262, 5592-5595.

De Azevedo, W. F., Jr.; Mueller-Diecicmann, H. J.; Schulze-Gahmen, U.; Worland, P. J.; Sausville, E. et al. Structural basis for specificity and potency of a flavonoid inhibitor of human CDK2, a cell cycle kinase. *Proc Natl Acad Sci USA* 1996, 93, 2735-2740.

Boumendjel, A.; Di Pietro, A.; Dumontet, C.; Barron, D. Recent advances in the discovery of flavonoids and analogs with high-affinity binding to P-glycoprotein responsible for cancer cell multidrug resistance. *Med Res Rev* 2002, 22, 512-529.

Conseil, G.; Baubichon-Cortay, H.; Dayan, G.; Jault, J. M.; Barron, D. et al. Flavonoids: a class of modulators with bifunctional interactions at vicinal ATP- and steroid-binding sites on mouse P-glycoprotein. *Proc Natl Acad Sci U S A* 1998, 95, 9831-9836.

Perez-Victoria, J. M.; Perez-Victoria, F. J.; Conseil, G; Maitrejean, M.; Comte, G. et al. High-affinity binding of silybin derivatives to the nucleotide-binding domain of a *Leishmania tropica* P-glycoprotein-like transporter and chemosensitization of a multidrugresistant parasite to daunomycin. *Antimicrob Agents Chemother* 2001, 45, 439-446.

Thiyagarajah, P.; Kuttan, S. C.; Lim, S. C.; Teo, T. S.; Das, N. P. Effect of myricetin and other flavonoids on the liver plasma membrane Cat+ pump. Kinetics and structure-function relationships. *Biochem Pharmacol* 1991. 41, 669-675.

Hirano, T.; Oka, K.; Akiba, M. Effects of synthetic and naturally occurring flavonoids on Na+,K+-ATPase: aspects of the structure-activity relationship and action mechanism. *Life Sci* 1989, 45, 1111-1117.

Jinsart, W.; Ternai, B.; Polya, G. M. Inhibition of rat liver cyclic AMP-dependent protein kinase by flavonoids. *Biol Chem Hoppe Seyler* 1992, 373, 205-211.

Ferriola, P. C.; Cody, V; Middleton, E., Jr. Protein kinase C inhibition by plant flavonoids. Kinetic mechanisms and structure-activity relationships. *Biochein Pharmacol* 1989, 38, 1617-1624.

Hagiwara, M.; Inoue, S.; Tanaka, T.; Nunoki, K.; Ito, M. et al. Differential effects of flavonoids as inhibitors of tyrosine protein kinases and serine/threonine protein kinases. *Biochem Pharmacol* 1988, 37, 2987-2992.

Perez-Victoria, J. M.; Chiquero, M. J.; Conseil, G.; Dayan, G.; Di Pietro, A. et al. Correlation between the affinity of flavonoids binding to the cytosolic site of *Leishmania tropica* multidrug transporter and their efficiency to revert parasite resistance to daunomycin. *Biochemistry* 1999, 38, 1736-1743.

Lo, A.; Burckart, G. J. P-glycoprotein and drug therapy in organ transplantation. *J Clin Pharniacol* 1999, 39, 995-1005.

Wang, R. B.; Kuo, C. L.; Lien, L. L.; Lien, E. J. Structure-activity relationship: analyses of p-glycoprotein substrates and inhibitors. *J Clin Pharm Ther* 2003, 28, 203-228.

Di Pietro, A.; Conseil, G; Perez-Victoria, J. M.; Dayan, G.; Baubichon-Cortay, H. et al. Modulation by flavonoids of cell multidrug resistance mediated by P-glycoprotein and related ABC transporters. *Cell Mol Life Sci* 2002, 59, 307-322.

Chambers, T. C.; Pohl, J.; Raynor, R. L.; Kuo, J. F. Identification of specific sites in human P-glycoprotein phosphorylated by protein kinase C. *J Biol Chemr* 1993, 268, 4592-4595.

Callaghan, R.; Higgins, C. F. Interaction of tamoxifen with the multidrug resistance P-glycoprotein. *Br J Cancer* 1995, 71, 294-299.

Smith, C. D.; Zilfou, J. T. Circumvention of P-glycoprotein-mediated multiple drug resistance by phosphorylation modulators is independent of protein kinases. *JBiol Chem* 1995, 270, 28145-28152.

Conseil, G.; Perez-Victoria, J. M.; Jault, J. M.; Gamarro, E; Goffeau, A. et al. Protein kinase C effectors bind to multidrug ABC transporters and inhibit their activity. *Biochemistry* 2001, 40, 2564-2571.

Dayan, G.; Jault, J. M.; Baubichon-Cortay, H.; Baggetto, L. G.; Renoir, J. M. et al. Binding of steroid modulators to recombinant cytosolic domain from mouse P-glycoprotein in close proximity to the ATP site. *Biochemistry* 1997, 36, 15208-15215.

Chen, H. X.; Bamberger, U.; Heckel, A.; Guo, X.; Cheng, Y. C. BIBW 22, a dipyridamole analogue, acts as a bifunctional modulator on tumor cells by influencing both P-glycoprotein and nucleoside transport. *Cancer Res* 1993, 53, 1974-1977.

Park, S. Y.; Lam, W.; Cheng, Y. C. X-ray repair cross-complementing gene 1 protein plays an important role in camptothecin resistance. *Cancer Res* 2002, 62, 459-465.

Lee, Y. et al., Increased Anti-P-glycoprotein Activity of Baicalein by Alkylation on the A Ring. J.Med. Chem. 2004. 47, 5555-5566.

\* cited by examiner

FIGURE 1 Scheme 1[a]
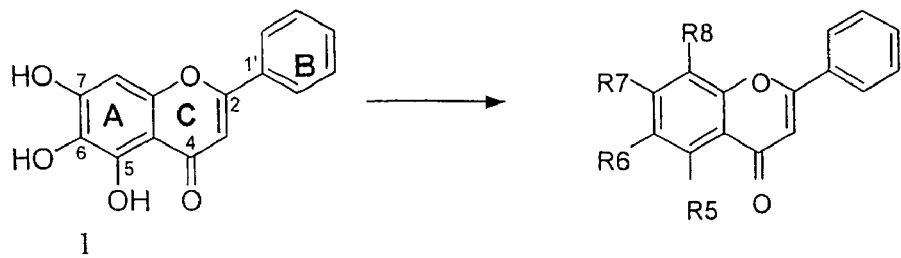
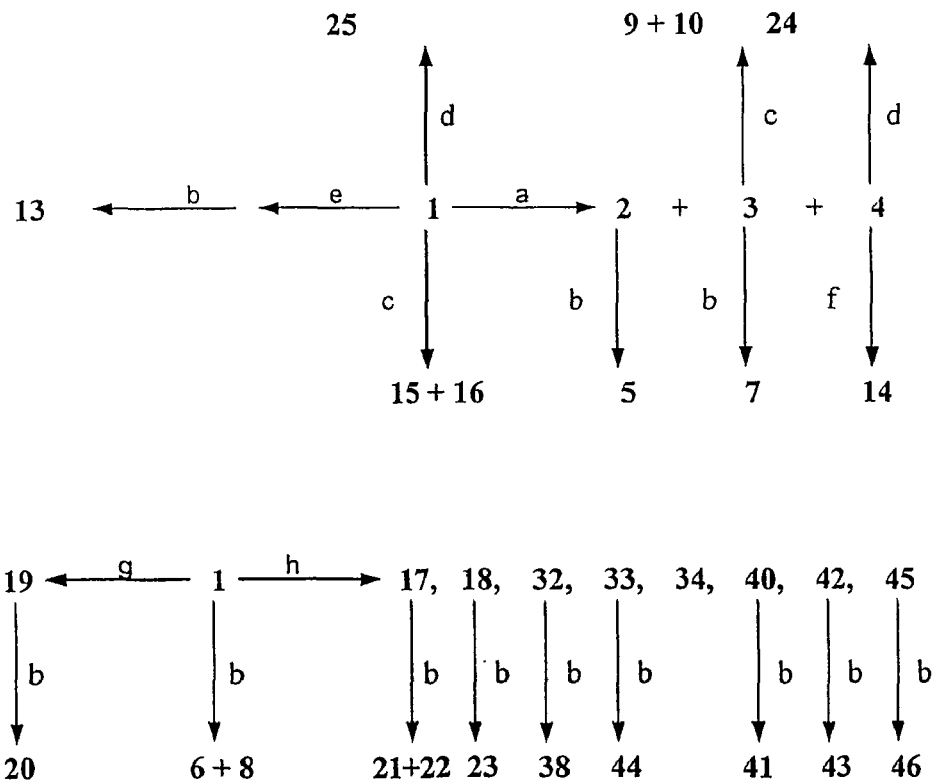
[a] Reagents and conditions: (a) $Ac_2O$, pyridine, rt; (b) $TMSCHN_2$, THF:MeOH (2:1), rt; (c) $K_2CO_3$, BnBr, acetone, reflux; (d) NBS, THF, conc $H_2SO_4$, rt; (e) $Ph_2CCl_2$, 170 °C; (f) $K_2CO_3$, KI, BnBr, acetone, reflux; (g) $Cs_2CO_3$, $BrCH_2Cl$, DMF, 50 °C; (h) $K_2CO_3$, $CH_3(CH_2)_nX$ (X=I or Br, n=1 for 32, 33, n=2 for 17, 18, n=3 for 45, n=4 for 40, n=5 for 42, n=7 for 34), acetone, reflux.

FIGURE 2

Table 1. Anti-P-gp activity and cytotoxicity of acetylated baicalein compounds.

| compd | functional group | | | | c log P[a] | anti-P-gp activity[b] | | cytotoxicity IC$_{50}$(μM) | |
|---|---|---|---|---|---|---|---|---|---|
| | R5 | R6 | R7 | R8 | | EC$_{50}$ (μM)[d] | A$_{max}$[c] | KB | KB/MDR |
| control | | | | | | | 0.5±0.1[f] | | |
| CSA | | | | | 2.9 | 1.2±0.3 | 3.5±0.3 | 0.6±0.2 | 1.5±0.7 |
| VRM | | | | | 4.5 | 14±1.2 | 2.2±0.1 | 19.6±2.7 | 51.7±4.7 |
| 1 | OH | OH | OH | H | 3.0 | 41±5.1 | 1.7±0.1 | 62.3±3.7 | 87.1±3.6 |
| 2 | OH | OAc | OH | H | 2.5 | 11±2.1 | 3.1±0.2 | 10.5±1.4 | 61.6±4.8 |
| 3 | OH | OAc | OAc | H | 2.4 | 9.7±1.8 | 2.6±0.1 | 12.7±2.3 | 69.3±6.4 |
| 4 | OAc | OAc | OAc | H | 1.2 | 6.8±0.7 | 3.0±0.2 | 14.5±2.1 | 57.2±7.3 |
| 7 | OMe | OAc | OAc | H | 1.7 | 12.3±1.5 | 2.9±0.1 | >100 | >100 |
| 5 | OMe | OAc | OMe | H | 2.3 | 11.5±1.1 | 2.4±0.1 | 85.5±8.5 | >100 |
| 24 | OH | OAc | OAc | Br | 3.1 | 15±3.1 | 1.8±0.3 | 12.4±2.7 | 16.2±2.3 |
| 25 | OH | OH | OH | Br | 3.7 | 15±2.9 | 1.8±0.2 | 14.1±1.4 | 18.7±3.1 |

Ac = acetyl and Me = methyl.

FIGURE 3

Table 2. Anti-P-gp activity and cytotoxicity of benzylated baicalein compounds.

| compd | functional group | | | | c log P | anti-P-gp activity[b] | | | cytotoxicity IC$_{50}$(μM) | |
|---|---|---|---|---|---|---|---|---|---|---|
| | R5 | R6 | R7 | R8 | | EC$_{50}$ (μM)[d] | | A$_{max}$[c] | KB | KB/MDR |
| control | | | | | | | | | | |
| CSA | | | | | | 1.2±0.3 | | 3.5±0.3 | 0.6±0.2 | 1.5±0.7 |
| VRM | | | | | | 14±1.2 | | 2.2±0.1 | 19.6±2.7 | 51.7±4.7 |
| 1 | OH | OH | OH | H | 2.9 | 41±5.1 | | 1.7±0.1 | 62.3±3.7 | 87.1±3.6 |
| 9 | OBn | OAc | OAc | H | 4.5 | 3.7±0.2 | | 3.6±0.2 | 11.3±1.7 | 12.2±1.1 |
| 10 | OH | OBn | OAc | H | 3.0 | 2.4±0.1 | | 2.8±0.1 | 16.3±2.1 | 18.3±2.3 |
| 14 | OAc | OAc | OBn | H | 3.5 | 1.1±0.1 | | 3.4±0.2 | 13.4±2.4 | 13.7±2.1 |
| 15 | OH | OBn | OH | H | 4.7 | 1.8±0.1 | | 3.7±0.2 | 4.3±1.6 | 3.2±1.2 |
| 16 | OH | OBn | OBn | H | 3.5 | 70±5.4 | | 1.1±0.1 | >100 | >100 |
| 13 | OMe | OCPh$_2$O | | H | 4.8 | 11.5±2.2 | | 1.9±0.1 | 60.5±5.5 | 40.6±3.4 |

A$_{max}$ value for control: 0.5±0.1[f]

Bn = benzyl, Me = methyl, and Ph = phenyl.

FIGURE 4

Table 3. Anti-P-gp activity and cytotoxicity of alkylated baicalein compounds.

| compd | R5 | R6 | R7 | R8 | c log P[a] | anti-P-gp activity[b] EC$_{50}$ (μM)[d] | $A_{max}$[c] | cytotoxicity IC$_{50}$(μM)[e] KB | KB/MDR |
|---|---|---|---|---|---|---|---|---|---|
| control |  |  |  |  |  |  | 0.5±0.1[f] |  |  |
| CSA |  |  |  |  | 2.9 | 1.2±0.3 | 3.5±0.3 | 0.6±0.2 | 1.5±0.7 |
| VRM |  |  |  |  | 4.5 | 14±1.2 | 2.2±0.1 | 19.6±2.7 | 51.7±4.7 |
| 1 | OH | OH | OH | H | 3.0 | 41±5.1 | 1.7±0.1 | 62.3±3.7 | 87.1±3.6 |
| 8 | OH | OMe | OMe | H | 3.5 | 4.6±1.1 | 3.4±0.3 | >100 | >100 |
| 6 | OMe | OMe | OMe | H | 2.9 | 5.5±0.4 | 2.7±0.2 | 85.9±7.8 | 57.9±5.9 |
| 19 | OH | OCH$_2$O | | H | 3.7 | 6.5±1.3 | 1.2±0.1 | >100 | >100 |
| 20 | OMe | OCH$_2$O | | H | 3.1 | 4.4±2.1 | 1.5±0.1 | >100 | >100 |
| 32 | OH | OEt | OH | H | 3.6 | 2.3±0.3 | 3.5±0.3 | 24.6±3.5 | 17.5±5.6 |
| 38 | OH | OEt | OMe | H | 4.1 | 1.5±0.3 | 2.3±0.2 | >100 | >100 |
| 33 | OH | OEt | OEt | H | 4.6 | 1.8±0.2 | 4.9±0.2 | >100 | >100 |
| 44 | OMe | OEt | OEt | H | 3.9 | 1.1±0.1 | 4.2±1.1 | 81.7±7.8 | 79.2±5.8 |
| 17 | OH | OPr | OH | H | 4.1 | 2±0.7 | 4.7±0.1 | 58.9±6.3 | >100 |
| 21 | OH | OPr | OMe | H | 4.6 | 1.2±0.4 | 4.6±0.1 | >100 | >100 |
| 22 | OMe | OPr | OMe | H | 3.9 | 1.7±0.1 | 4.6±0.1 | >100 | >100 |
| 18 | OH | OPr | OPr | H | 5.6 | 1.4±0.4 | 5.0±0.2 | >100 | >100 |
| 23 | OMe | OPr | OPr | H | 5.0 | 0.9±0.1 | 5.2±0.1 | 86.4±6.3 | 93.7±2.2 |
| 45 | OH | OC$_4$H$_9$ | OC$_4$H$_9$ | H | 6.7 | 1.5±0.3 | 3.2±0.1 | >100 | >100 |
| 46 | OMe | OC$_4$H$_9$ | OC$_4$H$_9$ | H | 6.1 | 1.6±0.2 | 4.4±0.1 | >100 | >100 |
| 40 | OH | OC$_5$H$_{11}$ | OC$_5$H$_{11}$ | H | 7.8 | 1.8±0.1 | 1.1±0.1 | >100 | >100 |
| 41 | OMe | OC$_5$H$_{11}$ | OC$_5$H$_{11}$ | H | 7.1 | 1.5±0.1 | 3.2±0.1 | 75.4±6.4 | 82.6±8.4 |
| 42 | OH | OC$_6$H$_{13}$ | OC$_6$H$_{13}$ | H | 8.8 | 1±0.1 | 1.0±0.1 | >100 | >100 |
| 43 | OMe | OC$_6$H$_{13}$ | OC$_6$H$_{13}$ | H | 8.2 | 1.3±0.2 | 1.1±0.1 | 39.1±8.5 | 44.8±7.9 |
| 34 | OH | OC$_8$H$_{17}$ | OC$_8$H$_{17}$ | H | 10.9 | 7.4±4.1 | 1.2±0.1 | >100 | >100 |

Me = methyl, Et = ethyl, Pr = n-propyl and Ph = phenyl.

COMPOUNDS AND METHODS TO INCREASE ANTI-P-GLYCOPROTEIN ACTIVITY OF BAICALEIN BY ALKYLATION ON THE A RING

RELATED APPLICATIONS

This application claims the benefit of priority of U.S. provisional application Ser. No. US60/541,443, filed Feb. 3, 2004, the entire contents of which is incorporated by reference herein.

FIELD OF THE INVENTION

The present invention is directed to analogs of baicalein which exhibit anti-P-glycoprotein activity and methods of enhancing the bioavailability of active compounds, especially orally administered compounds, by inhibition of P-glycoprotein 170 (P-gp 170) and/or CYP450 enzyme, especially CYP450 3A4 enzyme. Pharmaceutical compositions based upon these novel derivatives according to the present invention are also described herein.

BACKGROUND OF THE INVENTION

P-glycoprotein 170 (P-gp 170), a member of the ABC (ATP Binding Cassette) family, acts as an ATP-dependent drug efflux pump, preventing intracellular accumulation of miscellaneous drugs.[1,2] Overexpression of this protein is one of the mechanisms of multidrug resistance (MDR) of cancer cells. This protein is expressed in a cell- and tissue-specific manner, with high levels detectable in the kidney, liver, blood-brain barrier and lining of the intestine.[3] Studies using mdrl knockout mice and P-gp 170 tissue distribution in humans suggested several physiological roles of P-gp 170, including protection against toxic xenobiotics by blocking absorption by intestine; excretion of chemicals into bile duct or kidney tubule; prevention of chemicals taken into the brain through the blood-brain barrier; and efflux of steroid hormones and cholesterol from fesces.[2,4,5] Developing drugs to inhibit P-gp 170 activity is an important area of drug discovery. Such drugs could have use in facilitating the oral absorption of drugs through intestine, or the uptake of chemicals that are substrates of P-gp, into the brain. In addition, these compounds could also potentate the action of antitumor drugs, which are substrates of P-gp 170 in cancer cells that overexpress the P-gp 170 protein.

A large number of compounds with major structural differences have been found to act as inhibitors or substrates of P-gp 170: these include verapamil (VRM), a calcium channel antagonist; trifluoperazine, a calmodulin inhibitor; cyclosporin A (CSA), an immunosuppressant and progesterone, a steroid hormone. Verapamil has been examined clinically in combination with cancer chemotherapy.[6,7] However, the results were rather unsatisfactory due to high plasma drug levels, required to effectively reverse the MDR phenotype of cancer cells, which could cause cardiac toxicity. Compounds with higher potency against, and selectivity for, P-gp 170 are needed. A second generation of MDR reversal agents has emerged, and is based on the chemical modification of the first generation of inhibitors. Among these, dexniguldipine[8] and dexverapamil[9] were found to be more selective against P-gp 170, but they did not display improved potency. The acridonecarboxamide derivative GF120918 (GG918)[10] and the cyclosporin A analog PSC833[11] both displayed an activity that was 10-30 times more potent than the first generation of modulators, such as verapamil, tamoxifen and cyclosporin A.[12] A number of these compounds are currently under clinical evaluation.

Flavonoids are an important class of natural products found in plants. With its polyphenolic structure, this class of compounds has multiple actions, including interaction with estrogen receptor, free-radical scavenger, protein kinase inhibitor, NF-B inhibitor, P-gp 170 inhibitor, among others.[13] The biological activity found in herbal preparations is often attributed to its flavonoids. For example, the co-administration of grapefruit juice with various drugs has led to an increase in the plasma concentration of the drugs, which was attributed to the bioflavonoids found in the grapefruit juice.[14,15]

Flavonoids have also been shown to act on multiple targets with different specificity. For example, the flavonoid that binds to estrogen receptor requires hydroxyl groups at positions 2 and 3 of the B-ring, a double bond at positions 2-3 of the C-ring, and the absence of any hydrophobic prenylated substituent.[16] This is markedly different than the flavonoids that inhibit various ATPases or protein kinases. Recognition of the ATP binding pocket of these proteins requires the presence of three hydroxyl groups at positions 5 and 7 on the A-ring and position 3 of the C-ring, which favors some flavonols.[17] Moreover, some protein kinases exhibit different structural requirements for binding: an isoflavone structure has been demonstrated to inhibit tyrosine kinase activity,[18] and a flavone substituted at position 8 of A-ring with 4-(3-hydroxy-1-methylpiperidinyl) group has demonstrated activity against CDK2.[19] The inhibition of P-gp 170 by flavonoids has also been investigated and two binding modes have been postulated. The studies were performed using a truncated form of P-gp 170 in a membrane preparation from P-gp 170 overexpressing cells. The structural requirements for flavonoid activity have recently been summarized[20], and it appears that different classes of flavonoids have different structural requirements for inhibitory activity against P-gp 170.

In our previous study, we found that Radix scutellariae (Scute), a well-known Chinese herb, has inhibitory activity against P-gp 170. The active component of the Scute herb was found to be the natural product baicalein. However, the 7-glucuronosyl form of baicalein, which is the most abundant component of Scute, did not show anti-P-gp 170 activity. Other abundant Scute components, such as wogonoside and wogonin, were also found to lack inhibitory activity against P-gp 170 efflux action. Since baicalein (a 5,6,7-trihydroxyflavone) and wogonin (a 5,7-dihydroxy-8-methoxyflavone) have a very similar structure, this raised the possibility of an interesting structure-activity relationship of the flavone natural products for P-gp 170 inhibition.

In this study, we synthesized and evaluated a series of baicalein analogs, focusing on the substitution pattern at positions 5, 6, 7 and 8 of the A-ring. The results of this substitution show that alkoxyl groups on the A-ring of the flavone greatly increase the anti-P-gp 170 activity and alter their selectivity for the efflux pump.

OBJECTS OF THE INVENTION

It is an object of the invention to provide novel compounds which can be used to inhibit P-gp 170 and/or CYP450 in order to enhance the bioavailability of co-administered active agents.

It is an additional object of the invention to provide pharmaceutical compositions which comprise one or more compounds according to the invention and a pharmaceutically acceptable carrier, additive or excipient, optionally in combination with a bioactive agent the in vivo activity of which is diminished by P-gp 170 protein and/or CYP 450 enzyme.

It is yet another object of the invention to provide a method for enhancing the bioavailability of an active agent, the in vivo activity of which is diminished by the action of P-gp 170 protein and/or CYP 450 enzyme comprising co-administering an effective amount of one or more compounds according to the present in combination with a bioactive agent.

It is still another object of the invention to provide methods for inhibiting P-gp 170 protein or CYP 450 enzyme in patients.

These and/or other objects of the invention may be readily gleaned from a reading of the description of the invention which follows.

BRIEF DESCRIPTION OF THE FIGURES

FIG. 1 provides a general chemical synthetic scheme for the synthesis of compounds according the present invention. The legend is as follows:
[a]Reagents and conditions: (a) $Ac_2O$, pyridine, rt; (b) $TMSCHN_2$, THF:MeOH (2:1), rt; (c) $K_2CO_3$, BnBr, acetone, reflux; (d) NBS, THF, conc $H_2SO_4$, rt; (e) $Ph_2CCl_2$, 170° C.; (f) $K_2CO_3$, KI, BnBr, acetone, reflux; (g) $Cs_2CO_3$, $BrCH_2Cl$, DMF, 50° C.; (h) $K_2CO_3$, $CH_3(CH_2)_nX$ (X=I or Br, n=1 for 32, 33, n=2 for 17, 18, n=3 for 45, n=4 for 40, n=5 for 42, n=7 for 34), acetone, reflux.

FIGS. 2-4 (Tables 1-3) shows the biological activity of compounds according to the present invention, including anti-P-gp 170 activity as well as the cytotoxicity of the presently described compounds. Note that in many instances, compounds according to the present invention exhibit relatively low cytotoxicity. The legend for FIGS. 2-4 is as follows: [a]Using ChemDraw ULTRA, version 6.0.1, for 1-octanol/water system. [b]The anti-P-gp efflux activity is represented by intracellular vinblastine accumulation in 1 hr with or without drug treatment, see Experimental Section for details. [c]Maximum vinblastine accumulation (pmoles) of flavones (<100 μM) treated cells in the $10^6$ cells in 1 hr. [d]$EC_{50}$ calculated as the concentration that causes 50% of maximum vinblastine accumulation in the cells in 1 hr. [e]Cytotoxicity $IC_{50}$ calculated as the concentration required for 50% inhibition of cell growth, for each respective cell line, after 72 hr of drug exposure. [f]Control cells were treated with vinblastine only. All values represent the mean±SD of at least three identical experiments.

SUMMARY OF THE INVENTION

The present invention relates to compounds according to the formula:

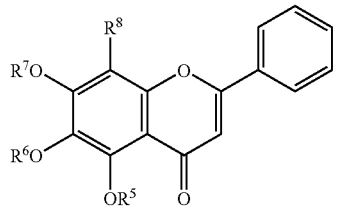

Where $R^5$ is H, an optionally substituted phenyl or benzyl group, an acyl group, preferably a $(C_2-C_{13})$acyl group, a $C_1-C_{20}$ alkyl or ether group, preferably a $(C_1-C_{12})$alkyl group, a phosphate, diphosphate, triphosphate or phosphodiester group;

$R^6$ and $R^7$ are each independently H, $(C_1-C_{12})$alkyl, $(C_2-C_{13})$acyl, or an optionally substituted phenyl or benzyl or together form a —$OCR^1R^2O$— group wherein each of $R^1$ and $R^2$ is independently H, a $C_1-C_3$ alkyl group or an optionally substituted phenyl or benzyl group; and $R^8$ is H, OH, an O-acyl group, preferably a $C_2-C_{13}$ O-acyl group, a $C_1-C_4$ alkyl or alkoxy group, F, Cl, Br or I, with the proviso that $R^5$, $R^6$, $R^7$ and $R^8$ are not all H, or a pharmaceutically acceptable salt thereof.

Pharmaceutical compositions according to the present invention comprise an effective amount of at least one compound as set forth above, optionally in combination with a pharmaceutically acceptable carrier, additive or excipient. Combination therapy (pharmaceuticals) comprising an effective amount of one or more of the above compounds in combination with an active agent, the activity of which is diminished by the action of P-gp 170 or CYP450, is a further aspect of the present invention.

Methods of enhancing the bioavailability or activity of active agents, the activity of which is diminished by P-gp 170 or CYP450, and in particular the 3A4 isozyme, comprising co-administering an effective amount of a compound according to the formula:

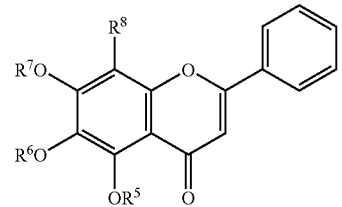

Where $R^5$ is H, an optionally substituted phenyl or benzyl group, an acyl group, preferably a $(C_2-C_{13})$acyl group, a $C_1-C_{20}$ alkyl or ether group, preferably a $(C_1-C_{12})$alkyl group, a phosphate, diphosphate, triphosphate or phosphodiester group;

$R^6$ and $R^7$ are each independently H, $(C_1-C_{12})$alkyl, $(C_2-C_{13})$acyl, or an optionally substituted phenyl or benzyl or together form a —$OCR^1R^2O$— group wherein each of $R^1$ and $R^2$ is independently H, a $C_1-C_3$ alkyl group or an optionally substituted phenyl or benzyl group; and $R^8$ is H, OH, an O-acyl group, preferably a $C_2-C_{13}$ O-acyl group, a $C_1-C_4$ alkyl or alkoxy group, F, Cl, Br or I, or a pharmaceutically acceptable salt thereof, in combination with said active agent. Methods of increasing the sensitivity of tumors/cancer to anti-cancer agents is another method aspect of the present invention.

Another aspect of the invention is directed to a method of inhibiting the action of P-gp 170 or CYP450 in a patient in need thereof comprising administering to said patient an effective amount of a compound according to the formula:

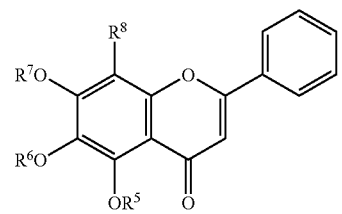

Where $R^5$ is H, $(C_1-C_{12})$alkyl, $(C_2-C_{13})$acyl, or an optionally substituted phenyl or benzyl group, an acyl group, a $C_1-C_{20}$ alkyl or ether group, a phosphate, diphosphate, triphosphate or phosphodiester group;

$R^6$ and $R^7$ are each independently H, $(C_1-C_{12})$alkyl, $(C_2-C_{13})$acyl, or an optionally substituted phenyl or benzyl or together form a —$OCR^1R^2O$— group wherein each of $R^1$ and $R^2$ is independently H or an optionally substituted phenyl or benzyl group; and $R^8$ is H, OH, an O-acyl group, preferably a $C_2-C_{13}$ O-acyl group, a $C_1-C_4$ alkyl or alkoxy group, F, Cl, Br or I, or a pharmaceutically acceptable salt thereof.

Another aspect of the invention relates to a method of treating multiple drug resistant tumors/cancer in a patient comprising co-administering an amount of a compound according to the present invention as described above in combination with all anti-tumor/anti-cancer agent.

DETAILED DESCRIPTION OF THE INVENTION

Definitions

Unless otherwise indicated, all terms used to describe the present invention, including scientific and technical terms, are to be given their conventional meaning as understood by those of ordinary skill practiced in the relevant art.

The term "patient" is used throughout the specification to describe an animal, preferably a human, to whom treatment with the compositions according to the present invention is provided. For treatment of those infections, conditions or disease states which are specific for a specific animal such as a human patient, the term patient refers to that specific animal.

The term "neoplasia" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, melanoma, acute lymphocytic leukemia, acute myelogenous leukemia, Ewing's sarcoma, small cell lung cancer, choriocarcinoma, rhabdomyosarcoma, Wilms' Tumor, neuroblastoma, hairy cell leukemia, mouth/pharynx, oesophagus, larynx, kidney, lymphoma, among others, which may be treated by one or more compounds according to the present invention.

The term "multiple drug resistant cancer" is used throughout the specification to describe a malignant tumor or other cancer containing cells which overexpress P-gp 170 protein and consequently, prevent anti-cancer agents and other bioactives from accumulating or reduce accumulation in those cells where they can produce their intended effect, whether that effect is to facilitate cell death, reduce or prevent cellular proliferation or otherwise impact the cancer cell's survival. Typical multiple drug resistant tumors/cancers which can be effectively treated using compounds according to the present invention include, for example, subgroups of virtually all tumors and cancer which exhibit multiple drug resistance phenotypes. Included among these tumors/cancer include most tumors which are derived from tissues which express P-gap 170, including most tumors of the adrenal gland, colon, kidney, liver, pancreas and acute myelogenous leukemia and numerous other cancers, including sarcomas, breast cancer, ovarian cancer, osteosarcomas, lymphomas, neuroblastomas, brain tumors, retinoblastoma, gastric and esophageal adenocarcinoma, renal cell carcinoma, acute lymphocytic leukemia, chronic myelogenous leukemia, among numerous others.

The term "effective amount" is used throughout the specification to describe an amount of the present compound or composition which is used to effect an intended result, within the context of its use. In the case of bioavailability enhancing agents this relates to the ability of the compound to enhance the bioavailability of a bioactive agent or drug which is co-administered to a patient, most often by inhibiting one or more of the P-gp 170 protein (also, "GP170 pump") or a CYP450 cytochrome 450 enzyme, and in particular CYP450 3A4 isozymes. In the case of anti-tumor/anti-cancer agents, and in particular, the treatment of multiple drug resistant cancers, an effective amount of these agents are used to inhibit p-gp 170 protein, with the intended effect of reducing the cancer cell's ability to expunge active agent and avoid accumulating agent which would destroy the cancer cell. In certain contexts, the term effective amount is used in conjunction with bioactive agents or drugs or the treatment of a condition or disease state in a patient to indicate an amount of agent which is effective for treating the condition or disease state, whether that treatment relates to central nervous system agents, or the the treatment of a patient suffering from neoplasia, in preferred embodiments, a cancerous tumor to prevent the further growth of the neoplasms- to bring that growth under control and preferably, produce a remission of the tumor.

The term "effective amount" with respect to traditional bioactive agents which are used to treat tumor/cancer is used throughout the specification to describe that amount of the compound according to the present invention which is administered to a mammalian patient, especially including a human patient, to reduce or inhibit the growth or spread of the cancer, and in certain preferred embodiments, a multiple drug resistant (MDR) tumor or cancer. Preferably, treatment with the compounds described in the present invention will result in a remission of the tumor/cancer including malignant hematogenous, ascitic or solid tumors. In the case of solid tumors, in certain preferred aspects, the compounds according to the present invention will inhibit the further growth of the tumor tissue and shrink the existing tumor.

The term "bioactive agent" or "drug" means any active agents, preferably, an orally active agent, which exerts a favorable biological effect in a patient and where increased concentration of the agent at the site of its activity is considered desirable. Bioactive agents include drugs and any number of compounds which produce a favorable pharmacological response in a patient. Preferably, bioactive agents according to the present invention include any one or more compounds which are drugs and which may be used to treat a condition or disease state in a patient, in particular, a human patient. Bioactive agents include a broad range of compounds including, for example, anesthetics, systemic antibiotics, antiparasitics, systemic quinolones, anti-infectives, anti-inflammatories, aminoglycosides, cephalosporins, penicillins, antidotes, anti-cholinesterases, metal poisoning antidotes, antineoplastics (antitumor and/or anticancer agents), cytotoxic agents, hormones, steroids, immunomodulators, cytokines, systemic antivirals, systemic antifungals, biologicals, alpha-antitrypsin, bone metabolism regulators, hypercalcemic agent, cardiovascular agents, beta blockers, cerebral vasodilators, cerebral metabolic enhancers, cholinesterase inhibitors, vasopressors, local diabetic agents, diagnostics such as CT scan enhancers and angiocardiography agents, adenosine deaminase deficiency agents, gonadotropin inhibitors, adrenal cortical steroid inhibitors, gonadotropin releasing hormone stimulant, urofollitropins, muscle relaxants such as neuromuscular blocking agents, prostaglandin analogs, prostaglandins, prostaglandin inhibitors, respiratory therapy agents, anticholinergics, beta andrenergic stimulators, sympathomimetics, and thrombolytics, antithrobotics, anticoagulants, antibiotics antiplatelet agents, thrombolytics, antiproliferatives, steroidal and nonsteroidal antiinflammatories, agents that inhibit hyperplasia and in particular restenosis, smooth muscle cell inhibitors, growth factors, growth factor inhibitors, cell adhesion inhibitors, cell adhesion promoters and drugs that may enhance the formation of healthy neointimal tissue, including endothelial cell regeneration agents, clonidine, estradiol, nicotine, nitroglycerin, and scopolamine, among numerous others. Others agents include antiinflammatory drugs, both steroidal (e.g., hydrocortisone, prednisolone, triamcinolone) and nonsteroidal (e.g., naproxen, piroxicam); antibacterials (e.g., penicillins such as penicillin V, cephalosporins such as cephalexin, erythromycin, tetracycline, gentamycin, sulfathiazole, nitrofurantoin, and quinolones such as norfloxacin, flumequine, and ibafloxacin); antiprotazoals (e.g., metronidazole); antifungals (e.g., nystatin); coronary vasodilators (e.g., nitroglycerin); calcium channel blockers (e.g., nifedipine, diltiazem); bronchodilators (e.g., theophylline, pirbuterol, salmeterol, isoproterenol); enzyme inhibitors such as collagenase inhibitors, protease inhibitors, elastase inhibitors, lipoxygenase inhibitors and angiotensin converting enzyme inhibitors (e.g., captopril, lisinopril); other antihypertensives (e.g., propranolol); leukotriene antagonists (e.g., ICI 204,219); anti-ulceratives such as H2 antagonists; steroidal hormones (e.g., progesterone, testosterone, estradiol, levonorgestrel); antivirals and/or immunomodulators (e.g., 1-isobutyl-1H-imidazo[4,5-c]quinolin-4-amine, 1-(2-hydroxy-2-methylpropyl)-1H-imidazo[4,5-c]quinoline-4-amine, and other compounds disclosed in U.S. Pat. No. 4,689,338, incorporated herein by reference, acyclovir); local anesthetics (e.g., benzocaine, propofol); cardiotoinics (e.g., digitalis, digoxin); antitussives (e.g., codeine, dextromethorphan); antihistamines (e.g., diphenhydramine, chlorpheniramine, terfenadine); narcotic analgesics (e.g., morphine, fentanyl); peptide hormones (e.g., human or animal growth hormones, LHRH); cardioactive products such as atriopeptides; proteinaceous products (e.g., insulin); enzymes (e.g., anti-plaque enzymes, lysozyme, dextranase); antinauseants (e.g., scopolomine); anticonvulsants (e.g., carbamazine); immunosuppressives (e.g., cyclosporine); psychotherapeutics (e.g., diazepam); sedatives (e.g., phenobarbital); hypnotics; anticoagulants (e.g., heparin); analgesics (e.g., acetaminophen); antimigraine agents (e.g., ergotamine, melatonin, sumatriptan); antiarrhythmic agents (e.g., flecainide); antiemetics (e.g., metaclopromide, ondansetron); anticancer agents (e.g., methotrexate); neurologic agents such as anxiolytic drugs; hemostatics; anti-obesity agents; antigout agents; antianxiety agents; antiinflammatory agents; hormones; immunosuppressive agents; hyplipedmic agents; antiparkinson agents; antifungal agents; analgesics; antimanic agents; antipyretics; antiarthritic agents; antiplatetet agents; anticonvulsants; antidiabetic agents, anticoagulants, antiarrhythmics, antianginal agents; and the like, as well as pharmaceutically acceptable salts, esters, solvates and clathrates thereof., among numerous others.

The term "antitumor" or "anticancer" agent is used to describe a bioactive agent which may be used to treat tumors and/or cancer. Although there are a large number of antitumor and anticancer agents which may be used in the present invention, antimetabolites, Ara C, etoposide, doxorubicin, daunorubicin, mitoxantrone, idarubicin, vinblastine, vincristine, taxol, hydroxyurea, colchicine, etoposide, tenoposide, actinomycin D, puromycin, valinomycin, mithramycin, gramicidin D, emetine, rhodamine 123, cytoxan, DiOC2, Hoechst 33342, mitomycin C, adriamycin, topotecan, campothecin, irinotecan, gemcitabine, cis-platin and mixtures, thereof are preferred agents for use in the present invention.

The term "co-administration", synonomyous with "concurrent administration", as used herein, refers to two active compounds that are administered at the same point in time (i.e, "simultaneous administration"), or sufficiently close in time so that the results of the two compounds together achieve a combined effect in the subject or patient. It is noted that co-administered agents may be administered at very different times, but the overall effect is such that activities of the two or more agents overlap and are combined to produce an intended effect.

The term "prevention" within context shall mean "reducing the likelihood" or preventing a condition or disease state from occurring as a consequence of administration or concurrent administration (co-administration) of one or more compounds or compositions according to the present invention, alone or in combination with another agent. It is noted here that within a population of subjects being treated with a bioactive agent in advance of a condition or disease state, a number will not be overcome by that condition or disease state as a consequence of such administration. Within the context of administration to a population of patients, such administration will reduce the likelihood that a condition or disease will occur in a given subject The term "pharmaceutically acceptable salt" is used throughout the specification to describe a salt form of one or more of the compositions (and in particularly preferred aspects according to the present invention, phosphate salts) herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of neoplasia, including cancer, the term "salt" shall mean a pharmaceutically acceptable salt, consistent with the use of the compounds as pharmaceutical agents.

The term "pharmaceutically acceptable derivative" is used throughout the specification to describe any pharmaceutically acceptable prodrug form (such as an ester or ether or other prodrug group) which, upon administration to a patient, provides directly or indirectly the present compound or an active metabolite of the present compound.

The term "alkyl" shall mean within its context a $C_1$-$C_{20}$, preferably a $C_1$-$C_{10}$ linear, branch-chained or cyclic fully saturated hydrocarbon radical. The term "ether" shall mean a $C_1$ to $C_{20}$ ether group, formed from an oxygen and an alkyl group at a position on the sugar moiety of compounds according to the present invention, or alternatively, may also contain at least one oxygen within the alkyl chain.

The term "acyl" is used throughout the specification to describe a group which contains a $C_1$ to $C_{20}$ linear, branched or cyclic alkyl chain bonded to a carbonyl group. The acyl group, in combination with the hydroxyl group results in an ester, which, in certain prodrug applications, after administration, may be cleaved to produce the free nucleoside form of the present invention. Acyl groups according to the present invention are represented by the structure:

where $R^4$ is a $C_1$ to $C_{20}$ linear, branched or cyclic alkyl group, alkoxyalkyl, aryloxyalkyl, such as phenoxymethyl, aryl, alkoxy, among others. Preferred acyl groups are those where $R^4$ is a $C_1$ to $C_{10}$ or a $C_1$-$C_{12}$, alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others including mesylate groups. One of ordinary skill in the art will recognize the acyl groups which will have utility in the present invention, either to synthesize the target pharmaceutical compounds or as prodrug of the nucleosides according to the present invention.

The term "phosphate ester" or "phosphodiester" is used throughout the specification to describe mono-phosphate groups at the $R^5$ position which are diesterified such that the phosphate group is rendered neutral, i.e., has a neutral charge. Phosphate esters for use in the present invention include those represented by the structures:

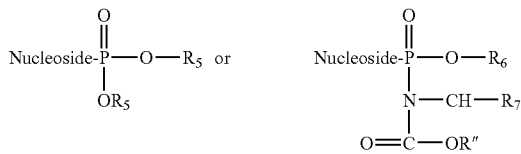

where $R_5$, R6 and R" are selected from a $C_1$ to $C_{20}$ linear, branched or cyclic alkyl group, alkoxyalkyl, aryloxyalkyl, such as phenoxymethyl, aryl and alkoxy, among others, and $R_7$ is a $C_1$ to $C_{20}$ linear, branched or cyclic alkyl or acyl group, alkoxyalkyl, aryloxyalkyl, such as phenoxymethyl, aryl and alkoxy, among others. Preferred monophosphate esters for use in prodrug forms according to the present invention are those where $R^5$ is a $C_1$ to $C_{20}$ is a linear or branched chain alkyl group, more preferably a $C_1$ to $C_3$ alkyl group.

The term "substituted" as it relates to phenyl or benzyl groups described herein, refers to one, two or three, OH, halogen (F, Cl, Br, I) or $C_1$-$C_3$ alkyl groups, preferably no more than one substituent, which may be substituted on the phenyl ring or the methylene or phenyl ring of the benzyl group.

The present invention relates to compounds, pharmaceutical compositions and methods of using these compounds to enhance the bioavailability of active agents or the sensitivity of tumors/cancer which are diminished by the action of P-gp 170 and/or CYP450, especially the 3A4 variant of CYP450 or to inhibit p-gp 170 and/or C"YP450.

Chemical synthesis of the present compounds may be afforded through readily available (most of them commercially available starting materials and intermediates). The compounds may be synthesized following the standard chemistry which is set forth in the following examples. Alternatively, one of ordinary skill will be able to readily modify known procedures for synthesizing and derivatizing benzopyran-4-one compounds to produce compounds according to the present invention. Oxidation, acylation, alkylation, halogenation reactions proceed following well-known reactions. Other reactions also follow well-known general synthetic methods. Those of ordinary skill will find no difficulty in synthesizing all of the presently described compounds.

The active compounds disclosed herein can, as noted above, can be used, within context, without modification or can be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; pr (b) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Pharmaceutical Formulations

The active compounds described above may be formulated for administration in a pharmaceutical carrier in accordance with known techniques. See, e.g., Remington, The Science And Practice of Pharmacy (9th Ed. 1995). In the manufacture of a pharmaceutical formulation according to the invention, the active compound (including the physiologically/pharmaceutically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

Although oral administration is the preferred route of administration, other routes of administration may also be contemplated for use in the present invention, including, rectal, topical, buccal (e.g., sub-lingual), vaginal, parenteral (e.g., subcutaneous, intramuscular, or intravenous), topical (i.e., both skin and mucosal surfaces, including airway surfaces) and transdermal administration, among others, although the most suitable route in any given case will depend on the nature and severity of the condition being treated and on the nature of the particular active compound which is being used. The most preferred route would be oral, co-administered with a bioactive agent, also delivered orally.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit/dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. The compound or salt is provided in the form of a lyophilizate which is capable of being reconstituted with a suitable pharmaceutically acceptable carrier to form a liquid composition suitable for injection thereof into a subject. The unit dosage form typically comprises from about 2 to 900 mg of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by, admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, Pharmaceutical Research 3 (6): 318 (1986)) and typically take the form of an optionally buffered aqueous solution of the active compound. Suitable formulations may comprise citrate or bis/tris buffer (pH 6) or ethanol/water and contain from 0.1 to 0.2 M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques. Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds disclosed above or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

Dosage

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art.

As a general proposition, a dosage from about 0.001 to about 15 mg/kg by weight of the patient, preferably from about 0.02 to about 5 mg/kg, will have therapeutic efficacy, with all weights being calculated based upon the weight of the active compound, including the cases where a salt is employed. Toxicity concerns at the higher level, especially for anti-tumor/anti-cancer agents may restrict intravenous dosages to a lower level such as up to about 5 mg/kg, with all weights being calculated based upon the weight of the active base, including the cases where a salt is employed. A dosage from about 0.001 mg/kg to about 10 mg/kg may be employed for oral administration. The administration of oral compositions is preferred, although parenteral administration of an anti-tumor/anti-cancer agent will reflect the typical administration of that agent. Typically, a dosage from about 0.5 mg/kg to 5 mg/kg may be employed for intramuscular injection. The frequency and duration of the treatment is usually once or twice per day as needed.

Chemistry

The synthesis of O-substituted baicalein derivatives from commercially available reagents was carried out using the general synthetic approach shown in Scheme 1, FIG. 1.

Acetylation of baicalein (1) with acetic anhydride was performed in pyridine to give mono-, di- and triacetylated derivatives 2-4. Baicalein was treated with benzyl bromide in dry acetone with potassium carbonate to provide mono- and dibenzylated analogues 15 and 16. The O-methylated derivatives 6 and 8 of baicalein were readily prepared by reaction with trimethylsilyldiazomethane (TMSCHN$_2$) in a methanolic TET solution at room temperature. Since the hydroxyl function on the C-5 position of baicalein makes an intramolecular hydrogen bond with the 4-keto group, it is resistant to alkylation and benzylation of baicalein occurred in the following order: 6>7>5.

The O-methylated products 6 and 8 of baicalein exhibited more potent anti-P-gp activities than that of baicalein itself. This finding led us to design and synthesize a series of alkylated baicalein analogues in order to examine their anti-P-gp activity. A variety of alkyl chains were attached to the hydroxyl groups in the baicalein A ring, and related flavonoids, through phenol alkylation with a number of alkyl halides.

The reaction of catechols on the baicalein A ring and flavonoids with bromochloromethane in DMF at 50° C. in the presence of cesium carbonate provided the corresponding methylenedioxy derivative 19. Similarly, compound 13 was readily prepared by heating baicalein at 170° C. for 1 h with dichlorodiphenylmethane then reaction with TMSCHN$_2$ in methanolic THF at room temperature.

The selective brominations at the C-8 position of baicalein and baicalein derivatives were performed directly with N-bromosuccinimide in the presence of a catalytic amount of concentrated sulfuric acid at room temperature.

Biological Results

In recent studies, the present inventors found that the anti-P-gp activity of *Scutellaria baicalensis Georgi* could inhibit P-gp 170 and have attributed this activity to the high quantity of baicalein (compound 1) found in the extract. We therefore synthesized a number of baicalein-related compounds in order to evaluate their structure-activity relationship against P-gp 170 activity. Since flavonoids could have multiple sites of action that affect cell growth, we also evaluated their growth inhibitory activity against KB, a human cancer cell line. If a compound exhibits cytotoxicity through the inhibition of cell function, in addition to serving as a substrate of P-gp 170, then the compound would be expected to demonstrate less activity against a cell line overexpressing P-gp 170, than the parent cell line. Therefore, we employed a multi-drug resistant cell line (KB/MDR) in addition to the parent KB cell line, in order to assess the susceptibility of a compound to act as a substrate or inhibitor of the P-gp 170 efflux pump. Our modification of the natural products focused primarily on the functional groups of the baicalein A ring, especially positions 5, 6 and 7, which might play a crucial role in P-gp 170 inhibition.

The KB/MDR cells, which overexpress human P-gp 170 protein, were used to evaluate the anti-P-gp 170 activity of drugs. In this manner, the intracellular amount of vinblastine, a substrate of P-gp 170 pump, was measured in the presence of the known P-gp inhibitors cyclosporin A and verapamil and compared to our synthetic flavones. The concentration of compound required to achieve 50% maximum accumulation of vinblastine is presented as the $EC_{50}$ value. The maximum accumulation of intracellular vinblastine caused by the compounds in one hour is expressed as $A_{max}$ (picomoles/$10^6$ cells). The cell growth inhibitory activity of compounds is presented as the concentration required to inhibit 50% growth of KB or KB/MDR cell lines ($IC_{50}$) following three days of compound treatment.

As shown in table 1 (FIG. 2), the number of acetoxy groups on the baicalein A ring altered the $EC_{50}$ of anti-P-gp activity. Compounds with one (2) or two (3) acetoxy groups on position 6 and 7 of the A ring exhibit an $EC_{50}$ that is one-fourth that of the parental compound. The activity of the flavone with three acetoxyl groups (4) at position 5, 6 and 7 did not differ from compound 2 or 3. The $A_{max}$ values of these three compounds were also similar, but higher than that found for baicalein. The flavones with acetoxy groups were more toxic to KB cells than the KB/MDR cells, indicating that the substitutions of hydroxyl groups by acetoxy could render the flavone a better substrate for P-gp 170 efflux pump. Substitution of the acetoxy groups in compound 4 with one (7) or two (5) methoxy groups did not alter the $EC_{50}$ or $A_{max}$ substantially, but increased the $IC_5$o value against cell growth. We also evaluated the impact of a bromo group on position 8 on anti-P-gp 170 efflux activity. Compound 25 (8-bromobaicalein) decreased the $EC_{50}$ to 15 □M, but the $A_{max}$ did not change, as compared to baicalein. Compound 24 (the 8-bromo derivative of compound 3) also showed less favorable activity against P-gp 170 activity than compound 3. Both of the compounds with an 8-bromo group were toxic to KB and KB/MDR cells, and showed the same $IC_{50}$ as compound 3 to KB cells, but lower that for the KB/MDR cells. This suggests that the bromo substitution prevents compound 3 from acting as a substrate of P-gp 170.

By adding one benzoxy group to the A ring of baicalein (Table 2, FIG. 3), the flavone became a very potent inhibitor of P-gp 170, irrespective of the position or the presence of other functional groups. All the flavones 6,7-Diacetoxy-5-benzoxyflavone (9), 7-Acetoxy-6-benzoxy-5-hydroxyflavone (10), 5,6-Diacetoxy-7-benzoxyflavone (14), and 6-benzoxy-5,7-dihydroxyflavone (15) exhibited a low $EC_{50}$ but higher $A_{max}$ in comparison with baicalein. On the other hand, the benzoxy group transformed the flavone a more toxic compound toward both KB and KB/MDR cells than baicalein. This suggests that these compounds have a different site of action in addition to P-gp 170, for which activity is not required to maintain cell growth. The fact that these compounds have the same $IC_{50}$ for KB and KB/MDR cells, suggests that they are inhibitors but not substrates of the P-gp 170 efflux pump. When the A ring of baicalein is substituted with two benzoxy groups, the flavone shows decreased cytotoxicity and anti-P-gp activity, without regard to being cyclic (13) or not (16).

Experimental results for the alkylated baicalein compounds are shown in Table 3. The introduction of a methoxy group onto the A ring decreased the $EC_{50}$ and increased the $A_{max}$. The presence of two (8) or three (6) methoxy groups on the A ring of baicalein dramatically increased the anti-P-gp activity, as evidenced by their $EC_{50}$ of 5.5 µM and 4.6 µM respectively, without a further increase in the $A_{max}$. Cyclizing the R6 and R7 position of the A ring decreased the cytotoxic activity and $A_{max}$, but did not alter the $EC_{50}$ against P-gp 170 activity as compared to compounds 8 and 6, regardless of whether the substitution at R5 is a hydroxy (19) or methoxy (20) group.

Alkyl substitution (methoxy) turned out to be a far more favorable substitution than either the acetoxy or benzoxy group for flavone anti-P-gp efflux activity. This is most likely due to the fact that this substitution prevents the compound from acting as a substrate for P-gp 170 or renders it less specific against P-gp 170. For this reason, we further explored the potential of this type of substitution in a search for an optimal linear alkoxy group. The ethoxy group was shown to be better than the methoxy group. The $EC_{50}$ values of 6-ethoxy-5,7-dihydroxyflavone (32) and 6,7-diethoxy-5-hydroxyflavone (33) were 2.3 µM and 1.8 µM, respectively, which is about the same as that of CSA. In addition, ethoxy compound 33 had a higher $A_{max}$ and less cytotoxicity than either CSA or compound 32. While there is no significant difference between one and two ethoxyl groups on the $EC_{50}$, there is a big difference in their cytotoxicity. Substitution of the R5 hydroxyl group in compound 33 with methoxy (44) did not change the $EC_{50}$ significantly. Substitution of the R7 ethoxy group of compound 33 with a methoxy (38) did not alter the $IC_{50}$ but did decrease the $A_{max}$.

Similar to the benzoxyl group substitution, presence of the propoxy substitution on any position of the A ring has significant effect on the potency and degree of anti-P-gp 170 efflux activity. One propoxy group on R6 (17) decreases the $EC_{50}$ to 2 µM, and increases the $A_{max}$ 9-fold higher than that of the control; two propoxyl groups on R6 and R7 (18) decreases the $EC_{50}$ to 1.4 M, and the $A_{ma}$ is 10-fold higher than the control. In addition, the $EC_{50}$ of 5-hydroxy-7-methoxy-6-propoxyflavone (21) was further decreased to 1.2 µM and the $A_{max}$ was 9-fold higher than that of the control. The molecule 5,7-dimethoxy-6-propoxyflavone (22), with an added methoxy on the R5 hydroxyl group, showed the same $EC_{50}$ and $A_{max}$ as compound 21. The cytotoxicity of 6,7-diethoxy-5-methoxyflavone (44) was higher than that of 6,7-diethoxy-5-hydroxyflavone (33), which only contains a single R5 position change from hydroxy to methoxy. The same phenomenon is found when comparing 5-hydroxy-6,7-dimethoxyflavone (8) to 5,6,7-trimethoxyflavone (6), compound 41 to 40 and compound 43 to 42. Finally, the most potent flavone in this series was found to be 5-methoxy-6,7-dipropoxyflavone (23), with two propoxy groups on R6 and R7 and a methoxy group on R5. The $EC_{50}$ of compound 23 was found to be 0.9 µM and the $A_{max}$ is 10-fold higher than that of the control. This is more efficient than CSA, which shows an activity that is 7-fold higher than control. The presence of methoxy group on the R5 position of compound 23, make it slightly more toxic than compound 18 to KB and KB/MDR cells, but this cytotoxicity is not altered in the presence of P-gp 170 activity, which suggests that compound 23 is not a substrate of P-gp 170. Compounds with alkoxy substitutions of longer chain length lead to a decrease in $A_{max}$, without altering the $EC_{50}$ substantially. No obvious correlation between a molecules' clog P value and anti-P-gp activity was observed.

Our previous studies have shown that flavone has the highest anti-P-gp activity among all of the flavonoid subclasses, which include flavone, flavonol, isoflavone, flavanone and glycosylated flavone. This conclusion is consistent with that observed by Gwenaelle Conseil, et al.[21] who demonstrated that the 2,3-double bond on C ring and the hydroxyl group on the A ring are important affinity determinants for flavonoid binding to P-gp. In addition, Jose M. Perez-victoria, et al.[22] showed that no matter how large the substituent group is made, it's effect is not as important as the 2,3-double bond in the C ring for binding affinity. The assay used in these studies, however, directly measured the binding affinity of the compounds for the cytosolic nucleotide-binding domain of P-gp 170 protein, which does not provide a measure for anti-P-gp 170 functional activity in living cells.

Ahcene Boumendjel et al.[20] incorporated modified chrysin in their studies and achieved results similar to our own. Their experiments showed that the increase in hydrophobicity of chrysin by alkylation with either methyl, isopropyl, benzyl, 3,3-dimethylallyl, or geranyl substituents was correlated with an increase in affinity for iii vitro binding to the P-gp cytosolic domain. Their anti-P-gp activity is therefore solely dependent on the number of isopropyl groups, irrespective of the position (6, 7, or 8) on the A ring. Our results indicate that the number of carbons permitted in the alkoxy group is preferably limited to three. Alkoxy groups in all three positions 5, 6 or 7 make a contribution to anti-P-gp activity. Potency is dependent on the alkoxyl group and deceases in the following order: propoxyl>ethoxyl>methoxyl. In our studies, all flavones with alkoxy groups have the same or better anti-P-gp activity than cyclosporin A (measured by vinblastine accumulation) and much higher than that of the flavones with c-alkyl groups, which only accumulate about 20-30% of drug as compared to cyclosporin A. The impact on anti-P-gp activity caused by n-propoxy substituents is greater than having c-isopropyl or c-dimethylallyl substituents on these compounds. Perhaps the high potency observed for their best compound, which has an o-dimethylallyl substitution pattern, results from the effect of oxygen alkylation and not from the dimethylallyl group itself. Moreover, the $A_{max}$ of compound 23 is 167% of cyclosporin A and 236% of verapamil. One possible interpretation of these results is that the alkoxyflavone is more specific for P-gp 170 and has no other cellular effect, which is not the case of cyclosporin A or verapamil. In this manner, it can reach a higher level of apparent anti-P-gp activity in the KB/MDR cells.

Interestingly, all of the flavones with an alkoxy group of 4-8 carbons exhibited the same level of $EC_{50}$ compared to compound 23, indicating that maybe the binding affinity of this series of alkoxyflavones remain the same, since the long chain substituents did not decrease the anti-P-gp activity. One possibility is that the long carbon chain of the alkoxyl group changes the orientation of the flavone (eg. insertion into plasma membrane) relative to the P-gp 170 binding site, so that they still bind to P-gp but do not block pump activity.

The benzyl group substituent also showed a large impact on anti-P-gp activity both in the studies of Ahcene Boumendjel's[20] and ours. The benzoxy group has much stronger effect on the $A_{max}$ than the benzyl group in both systems. On the other hand, both their and our benzoxy groups are connected to the A-ring at positions 6 and 7. With the same benzoxy group, the two acetoxy groups of our compound (5,6-diacetoxy-7-benzoxyflavone, the $A_{max}$ is 97% as compared to cyclosporin A) may have some supplementary effect compared to their compound (7-benzoxy-5-hydroxyflavone, the $A_{max}$ is 25% as compared to cyclosporin A). The addition of two benzoxyl groups on the A-ring, caused the flavone (6,7-dibenzoxy-5-hydroxyflavone) to lose all of its anti-P-gp activity in our experiments, but (6-benzyl-7-benzoxy-5-hydroxyflavone) showed an increase in both binding affinity and drug accumulation in their experiments. The only difference between these two molecules is the benzyl or benzoxyl group on position 6. It should also be noted that cytotoxicity increases greatly with benzoxy substitution on the A-ring.

In order to achieve a more comprehensive overview of the structure-activity relationship of the flavones, we subcategorized them based on the position of their substitutients. We first organized the same functional group on R6 and R7, in order to see the impact of R5 on anti-P-gp efflux activity. Compounds with the same substitutions on R6 and R7 were divided into four groups: compounds 3, 4, 7 and 9 with two acetoxy groups on R5 and R7; compound 8 and 6 with two methoxy groups; compound 33 and 44 with two ethoxy groups; and compound 18 and 23 with two propoxy groups on the R6 and R7 position. The $EC_{50}$ required to inhibit P-gp 170 activity of these four groups decrease in the following order: two acetoxys>two methoxys>two ethoxys>two propoxys. In addition, the change of R5 substituents is not as dominant as the change of the same two groups on the R6 and R7. The anti-P-gp activity of flavones with two acetoxy groups on R6 and R7 is dependent on the functional group in the R5 position. The anti-P-gp activity of flavones with two methoxy or ethoxy groups on R6 and R7 did not change with a change in the R5 functional group. Flavones with two propoxy groups on R6 and R7 were the most potent inhibitors in this series of compounds, regardless of whether the R5 is hydroxy or methoxy group. However, the methoxy group on the R5 position renders the flavones more toxic to cells as compared the hydroxyl group.

In the case of a fixed functional group on the R5 and R7 position, the molecules can be divided into three groups, those with two hydroxy groups (compounds 1, 2, 15, 17 and 32), two methoxy groups (compounds 5, 6 and 22), and a hydroxy group on the R5 and methoxy group on the R7 (compounds 8, 21 and 38). The anti-P-gp activity of the compounds with two hydroxyl groups was largely dependent on the functional group at the R6 position, from high (compounds 1 and 2) to very low (compounds 15 and 32) $EC_{50}$. The anti-P-gp efflux activity of compounds with two methoxy groups is also dependent on the functional group at the R6 position, showing both medium $EC_{50}$ (compounds 5 and 6) and very low (compound 22) activity. The anti-P-gp 170 activity of compounds with a hydroxy group on R5 and methoxy group on R7 do not show obvious dependence on the functional group at R6, since neither the methoxy ethoxy or propoxy groups changed the $EC_{50}$ value noticeably, however, all three were very good inhibitors. Their inhibitory effectiveness is shows the following decreasing order: propoxy (21)>ethoxy (38)>methoxy (8).

Compounds with the same functional groups on R5 and R6 could also be divided into four categories. With a hydroxy group on R5 and a benzoxy group on R6 (compounds 10 and 15), the $EC_{50}$ values decrease and are not affected by the substituent on R7, except the molecule containing two benzoxygroups (16), which lost both anti-P-gp 170 activity and cytotoxicity. The anti-P-gp 170 activity of compounds with a hydroxy group on R5 and an ethoxy group on R6 was not dependent on the functional group at R7 either (compounds 32, 38 and 33). The anti-P-gp 170 efflux activity of compounds with a hydroxy group on R5 and a propoxy group on R6 was also not dependent on the functional group at the R7 (compounds 17, 21 and 18). Even the anti-P-gp activity of the most potent compounds, containing a methoxy group on R5 and a propoxy group on R6 was not obviously dependent on the chemical function at R7 (compounds 22 and 23). It appears that small substituent changes on position 7 do not have an impact on anti-P-gp activity, however, large substituents at this position are not tolerated since baicalin (7-glucuronosyl baicalein), the most abundant chemical in the Scute, has no anti-P-gp activity.

The inhibition of P-gp 170 efflux activity itself should not cause cytotoxicity, and our data support this theory since their appears to be no correlation between p-gp inhibition and cytotoxicity in the compounds evaluated in this study. (Yes, This is true!) Therefore, the increased toxicity noted in some of the molecules is likely due to affinity of the compounds for additional biochemical targets with ATP-binding sites. Several flavonoids have been reported to be good inhibitors for a variety of ATP-binding proteins such as plasma membrane ATPases,[23,24] protein kinase A,[25] protein kinase C,[26] serine/threonine protein kinases,[27] tyrosine protein kinase[28] and topoisomerase II.[29] Staurosporine produces high intrinsic cytotoxicity in human cells in addition to its anti-P-gp activity. Based on a structural analysis, R. B. Wang et al.[30] suggested that the isobenzopyrrolidone of staurosporine meets the binding requirement of the adenosine moiety of ATP and prevents ATP binding to the ATP-binding site. In this comparison, however, the A ring of galangin (3,5,7-trihydroxyflavone) does not overlap well with the 5-member ring of adenosine, and that's the reason galangin does not exhibit cytotoxicity as staurosporine analog. A. D. Pietro et al.[31] indicated that among a total of 29 flavonoids examined, only three flavonols were found to bind to the ATP-binding site, and the hydroxyl group at position 3 of the flavonol is critical for binding. This requirement is similar to that observed for quercetin binding to the Hck tyrosine kinase, as demonstrated by cocrystallization[32] and for other ATPases by inhibition kinetics.[33] Based on these observations, most of our synthetic flavones are unlikely to be good candidates for ATP-binding site affinity because they lacking the hydroxyl group on R3, except the benzoxyflavone which could potentially block ATP binding by fitting to the adenine site in the ATP-binding pocket like staurosporine.

When a benzoxy group is connected to the A-ring of baicalein, its structure resembles L868276 (5, 7-dihydroxy-8-[4-(3-hydroxy-1-methyl)piperidinyl]-flavone), which fits nicely to the adenine-binding pocket of CDK2,[19] and this may be a source of its increased cytotoxicity. Interestingly, the cytotoxicity is lost when we add another benzoxyl group to the A-ring of baicalein. This is similar to a pattern noted with staurosporine modification, the addition of one benzyl group causes a decrease in cytotoxicity (CGP4125 1)[34] and adding another totally abolishes the cytotoxic effect (CGP42700).[35] It is possible that the increased steric bulk added to molecule by virtue the second benzyl group render the compounds incapable of entering the adenine-binding pocket of CDK2 due to steric hindrance. We are currently evaluating this hypothesis.

The nucleotide binding site of P-glycoprotein contains a region that interacts with hydrophobic steroid derivatives, such as RU486, called the steroid binding hydrophobic region (SBHR). This region is most likely located in close proximity to the ATP binding site since RU486 completely prevents or displaces the hydrophobic nucleotide derivative, 2(3)-methylanthraniloyl-ATP (MANT-ATP).[36] A tentative model for the interaction of flavonoids with P-glycoprotein and related multidrug transporters has been proposed by A. D. Pietro et al[31] Galangin (5,7-dihydroxyflavonol), kaempferol (4',5,7-trihydroxyflavone), kaempferide (3,5,7-trihydroxy-4'-methoxyflavone) and dehydrosilybin (3,5,7-trihydroxy-3'-monolignolflavone) appear to interact with the cytosolic nucleoside binding domain; the hydroxyl groups at positions 3 and 5, in addition to the ketone at position 4, are proposed to bind the ATP-binding site, whereas other parts of the molecules bind in the vicinal SBHR region. Prenylation of the A-ring would therefore increase the hydrophobic interactions with both the cytosolic steroid-interacting region and the drug-binding site. This would potentially produce a significant shift in flavonoid positioning, in such a way that overlap with the ATP binding site can no longer occur. Such a prenyl-flavonoid positioning appears to be efficient enough to directly inhibit P-gp 170 substrate binding and transport, while indirectly interfering with ATP hydrolysis and energy transduction. In our case, flavones without the 3-hydroxyl group may be acting in a similar fashion, since the alkoxyl group helps trihydroxyflavone (baicalein) to be a better P-gp modulator with less cytotoxicity and may be interacting with the steroid binding hydrophobic region of P-gp rather than the ATP-binding site. Benzoxyflavone, on the other hand, may likely be overlapping the ATP-binding site in order to decrease the efflux of P-gp 170 substrates such as vinblastine, and be exhibitng a high intrinsic cytotoxicity through interaction with the ATP-binding sites of other vital proteins.

In conclusion, acetylation, alkylation, or benzylation of hydroxyl groups on the A ring of baicalein can enhance interaction with the P-gp 170 protein and prevent its substrate efflux activity. The mode of interaction with these modified flavones appear be quite different, given the broad range of differences noted in $EC_{50}$, $A_{max}$ and cytotoxicity. The alkoxyflavones may interact with P-gp at a site other than the ATP-binding site, whereas the other modified flavonoids likely mimic the adenosine moiety of ATP and block the ATP-binding site. This suggests that the alkoxyflavones may have a lower propensity to interact with the ATP-binding site of other proteins, as observed by their lower cytotoxicity. In summary, the alkoxyflavones appear to be quite promising modulators of P-gp 170 function and warrant further exploration.

It is to be understood by those skilled in the art that the foregoing description and examples are illustrative of practicing the present invention, but are in no way limiting. Variations of the detail presented herein may be made without departing from the spirit and scope of the present invention as defined by the following claims.

EXAMPLES

General Chemistry Methods. All solvents and reagents were obtained from commercial suppliers and were used without further purification. Unless otherwise specified, reactions were performed under a nitrogen atmosphere with exclusion of moisture. All reaction mixtures were magnetically stirred and monitored by TLC using Si25OF precoated plates from J. T. Baker (0.25 mm). Flash column chromatography was performed on 32-63 D 60 Å silica gel from ICN SiliTech (ICN Biomedicals GmbH). Melting points were determined with an Electrothermal capillary melting point apparatus and are uncorrected. $^1$H NMR spectra were recorded on a Bruker AM-400 or GE QE-plus 300 spectrometer. Chemical shifts are reported using chloroform-d (δ 7.24 ppm) or DMSO-$d_6$ (2.50 ppm). All coupling constants are described in Hz. Mass spectra were conducted at the Mass Spectrometry Laboratory of the University of Illinois.

6-Acetoxy-5,7-dihydroxyflavone (2). Baicalein 1 (54 mg, 0.2 mmol) was dissolved in acetic anhydride (1 mL) and pyridine (1 mL), and the solution was stirred at room temperature for 2 h. The reaction mixture was poured into ice-water (10 mL), and the precipitate was collected by filtration and purified by flash chromatography on a column of silica gel eluted with $CH_2Cl_2$/MeOH (20:1) to yield compound 2 (35 mg, 56%) as a yellow powder. mp 205-207 ° C.; $^1$H NMR (DMSO-$d_6$) δ 2.28 (s, 3H, H1a), 6.67 (s, 1H, H3), 7.01 (s, 1H, H8), 7.57 (m, 3H, H3'+H4'+H5'), 8.79 (m, 2H, H2'+H6'), 11.28 (s, 1H, 7OH), 12.97 (s, 1H, 5OH); MS (EI) m/z 312 [M]$^+$, 270 (base).

6,7-Diacetoxy-5-hydroxyflavone (3) and 5,6,7-Triacetoxyflavone (4). Baicalein 1 (216 mg, 0.8 mmol) was dissolved in acetic anhydride (40 mL) and pyridine (12 mL), and the solution was stirred at room temperature for 48 h. The reaction mixture was poured into ice-water (100 mL), and the precipitate was collected by filtration and purified by flash chromatography on a column of silica gel eluted with $CH_2Cl2$/MeOH (40:1) to give compounds 3 (72 mg, 25%) and 4 (220 mg, 69%) as a pale yellow powder, respectively. (3): mp 204-206° C.; $^1$H NMR (CDCl$_3$) δ 2.36 (s, 6H, H1a+H1b), 6.74 (s, 1H, H3), 6.98 (s, 1H, H8), 7.55 (m, 3H, H3'+H4'+H5'), 7.89 (m, 2H, H2'+H6'), 12.95 (s, 1H, 5OH); MS (EI) m/z 354 [M]$^+$, 312, 270 (base). (4): mp 194-195° C.; $^1$H NMR (CDCl$_3$) δ 2.36, 2.37, 2.46 (each s, 9H, H1a, H1b, H1c), 6.67 (s, 1H, H3), 7.52 (s, 1H, H8), 7.54 (m, 3H, H3'+H4'+H5'), 7.87 (m, 2H, H2'+H6'); MS (EI) m/z 396 [M]$^+$, 354, 312, 270 (base).

6-Acetoxy-5,7-dimethoxyflavone (5). To a stirred solution of 2 (25 mg, 0.08 mmol) in a mixture of MeOH (4 mL) and THF (8 mL) was added trimethylsilyldiazomethane (TMSCHN$_2$, 2M in hexanes, 0.4 mL, 0.8 mmol). The reaction mixture was stirred at room temperature for 12 h, and then evaporated. Flash chromatography of the residue, eluting with in-hexane/EtOAc (1:1), gave compound 5 (5 mg, 18%) as a pale yellow powder. mp 208-210° C.; $^1$H NMR (CDCl$_3$) δ 2.40 (s, 3H, H1a), 3.96 (s, 6H, H1b+H1c), 6.70 (s, 1H, H3), 6.88 (s, 1H, H8), 7.54 (m, 3H, H3'+H4'+H5'), 7.88 (m, 2H, H2'+H6'); MS (EI) m/z 340 [M]$^+$, 298, 280 (base).

5,6,7-Trimethoxyflavone (6). To a stirred solution of 1 (54 mg, 0.2 mmol) in a mixture of MeOH (6 mL) and THF (12 mL) was added TMSCHN$_2$ (2M in hexanes, 1.2 mL, 2.4 mmol). The reaction mixture was stirred at room temperature for 36 h, and evaporated. Flash chromatography of the residue, eluting with $CH_2Cl_2$/acetone (15:1), gave compound 6 (30 mg, 48%) as a pale yellow powder. mp 164-165° C.; $^1$H NMR (CDCl$_3$) δ 3.90, 3.97, 3.99 (each s, 9H, H1a, H1b, H1c), 6.67 (s, 1H, H3), 6.81 (s, 1H, H8), 7.50 (m, 3H, H3'+H4'+H5'), 7.86 (m, 2H, H2'+H6'); MS (EI) m/z 312 [M]$^+$, 297 (base).

6,7-Diacetoxy-5-methoxyflavone (7). To a stirred solution of 3 (25 mg, 0.07 mmol) in a mixture of MeOH (2 mL) and THF (4 mL) was added TMSCHN$_2$ (2M in hexanes, 0.21 mL, 0.42 mmol). The reaction mixture was stirred at room temperature for 12 h, and evaporated. Flash chromatography of the residue, eluting with $CH_2Cl_2$/acetone (30:1), gave compound 7 (6 mg, 23%) as a pale yellow powder. mp 240-242° C.; $^1$H NMR (CDCl$_3$) δ 2.35, 2.45 (each s, 6H, H1a, H1b), 3.95 (s, 3H, H1c), 6.61 (s, 1H, H3), 6.96 (s, 1H, H8), 7.52 (m, 3H, H3'+H4'+H5'), 7.85 (m, 2H, H2'+H6'); MS (EI) m/z 368 [M]$^+$, 326, 284 (base).

5-Hydroxy-6,7-dimethoxyflavone (8). To a stirred solution of 1 (54 mg, 0.2 mmol) in a mixture of MeOH (6 mL) and THF (12 mL) was added TMSCHN$_2$ (2M in hexanes, 0.6 mL, 1.2 mmol). The reaction mixture was stirred at room temperature for 8 h, and evaporated. Flash chromatography of the residue, eluting with CH$_2$Cl$_2$/acetone (40:1 to 20: 1), gave compound 8 (8 mg, 13%) as a pale yellow powder. mp 159-160° C.; $^1$H NMR (CDCl$_3$) δ 3.94, 3.99 (each s, 6H, H1a, H1b), 6.59 (s, 1H, H3), 6.70 (s, 1H, H8), 7.55 (m, 3H, H3'+H4'+H5'), 7.89 (m, 2H, H2'+H6'); MS (EI) m/z 298 ([M]$^+$, base), 283.

6,7-Diacetoxy-5-(benzoxy)flavone (9) and 7-Acetoxy-6-(benzoxy)-5-hydroxyflavone (10). A mixture of 3 (21 mg, 0.06 mmol), benzyl bromide (0.03 mL), and anhydrous K$_2$CO$_3$ (26 mg) in acetone (15 mL) was refluxed for 8 h with stirring. The reaction mixture was filtered, and the solvent was evaporated under reduced pressure. Flash chromatography of the residue, eluting with n-hexane/EtOAc (3:2), afforded compounds 9 (18 mg, 68%) and 10 (8 mg, 33%) as a pale yellow powder, respectively. (9): mp 175-177° C.; $^1$H NMR (CDCl$_3$) δ 2.32, 2.47 (each s, 6H, H1a, H1b), 5.22 (s, 2H, H7c), 6.61 (s, 1H, H3), 7.02 (s, 1H, H8), 7.42 (m, 5H, H2c+H3c+H4c+H5c+H6c), 7.52 (m, 3H, H3'+H4'+H5'), 7.84 (m, 2H, H2'+H6'); MS (EI) m/z 444 [M]$^+$, 402, 360, 269 (base) (10): mp 184-185° C.; $^1$H NMR (CDCl$_3$) δ 2.37 (s, 3H, H1b), 5.22 (s, 2H, H7a), 6.64 (s, 1H, H3), 6.70 (s, 1H, H8), 7.42 (m, 5H, H2a+H3a+H4a+H5a+H6a), 7.55 (m, 3H, H3'+H4'+H5'), 7.88 (m, 2H, H2'+H6'), 13.00 (s, 1H, 5OH); MS (EI) m/z 402 [M]$^+$, 360, 269 (base).

6,7-(Diphenylmethylenedioxy)-5-methoxyflavone (13). A mixture of 1 (27 mg, 0.1 mmol) and dichlorodiphenylmethane (0.02 mL, 0.1 mmol) was stirred under nitrogen at 170° C. for 1 h. The reaction mixture was cooled to 30° C. and then dissolved in a minimum amount of CH$_2$Cl$_2$. The crude product was purified by flash chromatography on a column of silica gel eluted with CH$_2$Cl$_2$ to yield compound 11 (35 mg, 81%). To a stirred solution of 11 (14 mg, 0.03 mmol) in a mixture of MeOH (2 mL) and THF (4 mL) was added TMSCHN$_2$ (2M in hexanes, 0.1 mL, 0.2 mmol). The reaction mixture was stirred at room temperature for 24 h, and then evaporated. Flash chromatography of the residue, eluting with CH$_2$Cl$_2$/MeOH (40:1), gave compound 13 (13 mg, 90%) as a pale yellow powder. mp 238-240° C.; $^1$ NMR (CDCl$_3$) δ 4.24 (s, 3H, H1c), 6.67 (s, 1H, H3), 6.81 (s, 1H, H8), 7.42 (m, 6H, H3a+H4a+H5a+H3b+H4b+H5b), 7.50 (m, 3H, H3'+H4'+H5'), 7.61 (m, 4H, H2a+H6a+H2b+H6b), 7.85 (m, 2H, H2'+H6'); MS (EI) m/z 448 [M]$^+$, 402, 371, 266, 167 (base).

5,6Diacetoxy-7-(benzoxy)flavone (14). A mixture of 4 (34 mg, 0.086 mmol), benzyl bromide (0.05 mL), KI (3.5 mg), and anhydrous K$_2$CO$_3$ (30 mg) in acetone (15 mL) was refluxed for 24 h with stirring. The reaction mixture was filtered, and the solvent was evaporated under reduced pressure. Flash chromatography of the residue, eluting with n-hexane/EtOAc (3:2), afforded compound 14 (20 mg, 52%) as a white solid. mp 174-175° C.; $^1$H NMR (CDCl$_3$) δ 2.27, 2.48 (each s, 6H, H1a, H1c), 5.14 (s, 2H, H7b), 6.53 (s, 1H, H3), 6.97 (s, 1H, H8), 7.38 (m, 5H, H2b+H3b+H4b+H5b+H6b), 7.47 (m, 3H, m, H3'+H4'+H5'), 7.76 (m, 2H, H2'+H6'); MS (EI) m/z 444 [M]$^+$, 402, 360, 269 (base).

6-(Benzoxy)-5,7-dihydroxyflavone (15) and 6,7-(Dibenzoxy)-5-hydroxy-flavone (16). A mixture of 1 (54 mg, 0.2 mmol), benzyl bromide (0.12 mL), and anhydrous K$_2$CO$_3$ (83 mg) in acetone (15 mL) was refluxed for 8 h with stirring. The reaction mixture was filtered, and the solvent was evaporated under reduced pressure. Flash chromatography of the residue, eluting with CH$_2$Cl$_2$/MeOH (100:1 to 50:1), afforded compound 15 (30 mg, 42%) as a yellow powder and compound 16 (24 mg, 27%) as a pale yellow powder. (15): mp 195-197° C.; $^1$H NMR (CDCl$_3$) δ 5.27 (s, 2H, H7a), 6.67 (s, 2H, H3 +H8), 7.44 (m, 5H, H2a+H3a+H4a+H5a+H6a), 7.52 (m, 3H, H3'+H4'+H5'), 7.88 (m, 2H, H2'+H6'); MS(EI) m/z 360 [M]$^+$, 269 (base). (16): mp 191-193° C.; $^1$H NMR (CDCl$_3$) δ 5.17, 5.19 (each s, 4H, H7a, H7b), 6.59 (s, 1H, H3), 6.69 (s, 1H, H8), 7.30-7.55 (m, 13H, H3'+H4'+H5'+H2a+H3a+H4a+H5a+H6a+H2b+H3b+H4b+H5b+H6b), 7.87 (m, 2H, H2'+H6'); MS (EI) m/z 450 [M]$^+$, 359, 269, 91 (base).

5,7-Dihydroxy-6-propoxyflavone (17) and 5-Hydroxy-6,7-dipropoxyflavone (18). A mixture of 1 (54 mg, 0.2 mmol), n-propyl iodide (0.06 mL), and anhydrous K$_2$CO$_3$ (110 mg) in acetone (20 mL) was refluxed with stirring for 24 h. The reaction mixture was concentrated under reduced pressure, diluted with water (30 mL) and extracted with CH$_2$Cl$_2$ (3×30 mL). The extract was washed with water and dried over MgSO$_4$, and the solvent was evaporated in vacuo. The residue was purified by flash chromatography on a column of silica gel eluted with CH$_2$Cl$_2$/MeOH (70:1 to 50:1) to yield compounds 17 (7 mg, 11%) and 18 (44 mg, 62%) as a yellow powder, respectively. (17): mp 162-163° C.; $^1$H NMR (CDCl$_3$) δ 1.11 (t, 3H, H3a, J=7.5 Hz), 1.95 (sextet, 2H, H2a, J=7.5 Hz), 4.13 (t, 2H, H1a, J=7.5 Hz), 6.62 (s, 1H, H3), 6.69 (s, 1H, H8), 7.54 (m, 3H, H3'+H4'+H5'), 7.90 (m, 2H, H2'+H6'); MS (EI) m/z 312 [M]$^+$, 297, 283, 270 (base). (18): mp 89-91° C.; $^1$H NMR (CDCl$_3$) δ 1.07, 1.11 (each t, 6H, H3a, H3b, J=7.5 Hz), 1.82, 1.92 (each sextet, 4H, H2a, H2b, J=7.5 Hz), 4.02, 4.05 (each t, 4H, H1a, H1b, J=7.5 Hz), 6.54 (s, 1H, H3), 6.66 (s, 1H, H8), 7.53 (m, 3H, H3'+H4'+H5'), 7.88 (m, 2H, H2'+H6'); MS (EI) m/z 354 ([M]$^+$, base), 325, 311, 283, 270.

5-Hydroxy-6,7-(methylenedioxy)flavone (19). A mixture of 1 (81 mg, 0.3 mmol) and cesium carbonate (244 mg, 0.75 mmol) in DMF (5 mL) was stirred at room temperature for 30 min. Bromochloromethane (0.05 mL, 0.75 mmol) was added to the DMF solution, and the mixture was stirred at 50° C. for 8 h then diluted with CH$_2$Cl$_2$. The dichloromethane solution was washed with water and brine, dried over MgSO$_4$, filtered, and concentrated in vacuo. The residue was purified by flash chromatography on a column of silica gel eluted with CH$_2$Cl$_2$/MeOH (100:1 to 50:1) to give compound 19 (29 mg, 33%) as a pale yellow powder. mp 213-215° C.; $^1$H NMR (CDCl$_3$) δ 6.12 (s, 2H, H1a), 6.61 (s, 1H, H3), 6.70 (s, 1H, H8), 7.55 (m, 3H, H3'+H4'+H5'), 7.87 (m, 2H, H2'+H6'); MS (EI) m/z 282 ([M]$^+$, base), 149.

5-Methoxy-6,7-(methylenedioxy)flavone (20). To a stirred solution of 19 (17 mg, 0.06 mmol) in a mixture of MeOH (3 mL) and THF (6 mL) was added TMSCHN$_2$ (2M in hexanes, 0.3 mL, 0.6 mmol). The reaction mixture was stirred at room temperature for 24 h and evaporated. Flash chromatography of the residue, eluting with CH$_2$Cl$_2$/acetone (30:1), afforded compound 20 (12 mg, 68%) as a white solid. mp 202-204° C.; $^1$H NMR (CDCl$_3$) δ 4.14 (s, 3H, H1b), 6.08 (s, 2H, H1a), 6.71 (s, 1H, H3), 6.75 (s, 1H, H8), 7.51 (m, 3H, H3'+H4'+H5'), 7.86 (m, 2H, H2'+H6'); MS (EI) m/z 296 [M]$^+$, 268 (base), 250.

5-Hydroxy-7-methoxy-6-propoxyflavone (21) and 5,7-Dimethoxy-6-propoxy-flavone (22). To a stirred solution of 17 (19 mg, 0.06 mmol) in a mixture of MeOH (4 mL) and THF (8 mL) was added TMSCHN$_2$ (2M in hexanes, 0.2 mL, 0.4 mmol). The reaction mixture was stirred at room temperature for 24 h and evaporated. Flash chromatography of the residue, eluting with $CH_2Cl_2$/MeOH (30:1), gave compound 21 (4 mg, 20%) as a yellow powder and compound 22 (9.2 mg, 45%) as a pale yellow powder. (21): mp 112-113° C.; $^1H$ NMR ($CDCl_3$) δ 1.12 (t, 3H, H3a, J=7.5 Hz), 1.95 (sextet, 2H, H2a, J=7.5 Hz), 3.93 (s, 3H, H1b), 4.09 (t, 2H, H1a, J=7.5 Hz), 6.57 (s, 1H, H3), 6.69 (s, 1H, H8), 7.55 (m, 3H, H3'+H4'+H5'), 7.90 (m, 2H, H2'+H6'); MS (EI) m/z 326 ([M]$^+$, base), 283, 269. (22): mp 135-136° C.; $^1H$ NMR ($CDCl_3$) δ 1.13 (t, 3H, H3a, J=7.5 Hz), 1.96 (sextet, 2H, H2a, J=7.5 Hz), 3.92, 4.01 (each s, 6H, H1b, H1c), 4.09 (t, 2H, H1a, J=7.5 Hz), 6.73 (s, 1H, H3), 6.82 (s, 1H, H8), 7.52 (m, 3H, H3'+H4'+H5'), 7.89 (m, 2H, H2'+H6'); MS (EI) m/z 340 [M]$^+$, 325 (base), 283.

5-Methoxy-6,7-dipropoxyflavone (23). To a stirred solution of 18 (28 mg, 0.08 mmol) in a mixture of MeOH (4 mL) and TH:F (8 mL) was added $TMSCHN_2$ (2M in hexanes, 0.32 mL, 0.64 mmol). The reaction mixture was stirred at room temperature for 24 h and evaporated. Flash chromatography of the residue, eluting with $CH_2Cl_2$/acetone (15:1), gave compound 23 (23 mg, 78%) as a pale yellow powder. mp 109-110° C.; $^1$HNMR($CDCl_3$) δ 1.08, 1.12 (each t, 6H, H3a, H3b, J=7.5Hz), 1.82, 1.95 (each sextet, 4H, H2a, H2b, J=7.5 Hz), 3.99 (s, 3H, H1c), 4.00, 4.06 (each t, 4H, H1a, H1b, J=7.5 Hz), 6.72 (s, 1H, H3), 6.81 (s, 1H, H8), 7.52 (m, 3H, H3'+H4'+H5'), 7.89 (m, 2H, H2'+H6'); MS (EI) m/z 368 [M]$^+$, 325 (base), 283.

6,7-Diacetoxy-8-bromo-5-hydroxyflavone (24). A mixture of 4 (84 mg, 0.21 mmol) and N-bromosuccinimide (NBS, 56 mg, 0.32 mmol) in THF (8 mL) and conc. $H_2SO_4$ (10 μL) was stirred at room temperature for 48 h. The reaction mixture was extracted with EtOAc, washed with 10% aqueous $NaHSO_4$ solution and water, dried over $MgSO_4$, and then concentrated in vacuo. The residue was recrystallized from MeOH to give compound 24 (50 mg, 55%) as a yellow powder. mp 244-246° C.; $^1H$ NMR ($CDCl_3$) δ 2.38, 2.44 (each s, 6H, H1a, H1b), 6.82 (s, 1H, H3), 7.59 (m, 3H, H3'+H4'+H5'), 8.01 (m, 2H, H2'+H6'); MS (EI) m/z 434 [M+2]$^+$, 432 [M]$^+$, 390, 348 (base), 270, 269.

8-Bromo-5,6,7-trihydroxyflavone (25). A mixture of 1 (35 mg, 0.13 mmol) and NBS (33 mg, 0.19 mmol) in THF (4 mL) and conc. $H_2SO4$ (5 μL) was stirred at room temperature for 12 h. The reaction mixture was extracted with EtOAc, washed with 10% aqueous $NaHSO_4$ solution and water, dried over $MgSO_4$, and then concentrated in vacuo. The residue was recrystallized from MeOH to give compound 25 (26 mg, 57%) as a yellow powder. mp 263-265° C.; $^1H$ NMR (DMSO-$d_6$) δ 7.07 (s, 1H, H3), 7.59 (m, 3H, H3'+H4'+H5'), 8.12 (m, 2H, H2'+H6'), 9.58, 10.92, 12.76 (each s, 3H, 5OH, 6OH, 7OH); MS (EI) m/z 350 [M+2]$^+$, 348 ([M]$^+$, base), 270.

6-Ethoxy-5,7-dihydroxyflavone (32) and 6,7-Diethoxy-5-hydroxyflavone (33). A mixture of 1 (81 mg, 0.3 mmol), ethyl iodide (0.07 mL), and anhydrous $K_2CO_3$ (166 mg) in acetone (25 mL) was refluxed with stirring for 18 h. The reaction mixture was concentrated under reduced pressure, diluted with water (50 mL) and extracted with $CH_2Cl_2$ (50 mL×3). The extract was washed with water, dried over $MgSO_4$ and the solvent evaporated in vacuo. The residue was purified by flash chromatography on a column of silica gel and eluted with $CH_2Cl_2$/MeOH (50:1) to give compounds 32 (30 mg, 34%) and 33 (12 mg, 12%) as a yellow powder, respectively. (32): mp 190-192° C.; $^1H$ NMR ($CDCl_3$) δ 1.55 (t, 3H, H2a, J=6.9 Hz), 4.23 (q, 2H, H1a, J=6.9 Hz), 6.60 (s, 1H, H3), 6.68 (s, 1H, H8), 7.53 (m, 3H, H3'+H4'+H5'), 7.89 (m, 2H, H2'+H6'), 12.50 (s, 1H, 5OH); MS (EI) m/z 298 ([M]$^+$, base), 283, 270, 269, 254. (33): mp 132-133° C.; $^1H$ NMR ($CDCl_3$) δ 1.41, 1.53 (each t, 6H, H2a, H2b, J=7.2 Hz), 4.13, 4.19 (each q, 4H, H1a, H1b, J=7.2 Hz), 6.55 (s, 1H, H3), 6.67 (s, 1H, H8), 7.54 (m, 3H, H3'+H4'+H5'), 7.89 (m, 2H, H2'+H6'), 12.65 (s, 1H, 5OH); MS (EI) m/z326 [M]$^+$, 311, 297 (base), 269.

5-Hydroxy-6,7-(dioctyloxy)flavone (34). A mixture of 1 (81 mg, 0.3 mmol), 1-iodooctane (0.16 mL), and anhydrous $K_2CO_3$ (166 mg) in acetone (25 mL) was refluxed with stirring for 30 h. The reaction mixture was concentrated under reduced pressure, diluted with water (50 mL) and extracted with $CH_2Cl_2$ (50 mL×3). The extract was washed with water and dried over $MgSO_4$, and the solvent was evaporated in vacuo. The residue was purified by flash chromatography on a column of silica gel and eluted with $CH_2Cl_2$/MeOH (100:1 to 50:1) to give compound 34 (122 mg, 82%) as a pale yellow powder. mp 85-86° C.; 1H NMR ($CDCl_3$) δ 0.89, 0.90 (each t, 6H, H8a, H8b, J=6.9 Hz), 1.31-1.52 (m, 2OH, H3a+H4a+H5a+H6a +H7a+H3b+H4b+H5b+H6b+H7b), 1.79, 1.89 (each t, 4H, H2a, H2b, J=6.9 Hz), 4.03, 4.07 (each t, 4H, H1a, H1b, J=6.9 Hz), 6.53 (s, 1H, H3), 6.64 (s, 1H, H8), 7.51 (m, H3, H3'+H4'+H5'), 7.86 (m, 2H, H2'+H6'), 12.45 (s, 1H, 5OH); MS (EI) m/Z 494 [M]$^+$, 382, 270 (base).

6-Ethoxy-5-hydroxy-7-methoxyflavone (38). To a stirred solution of 32 (10 mg, 0.034 mmol) in a mixture of MeOH (3 mL) and THF (6 mL) was added $TMSCHN_2$ (2M in hexanes, 0.02 mL, 0.04 mmol). The reaction mixture was stirred at room temperature for 24 h and evaporated. Flash chromatography of the residue, eluting with $CH_2Cl_2$/MeOH (50:1), afforded compound 38 (7.4 mg, 70%) as a pale yellow powder. mp 133-134° C.; $^1H$ NMR ($CDCl_3$) δ 1.55 (t, 3H, H2a, J=6.9 Hz), 3.93 (s, 3H, H1b), 4.21 (q, 2H, H1a, J=6.9 Hz), 6.57 (s, 1H, H3), 6.69 (s, 1H, H8), 7.56 (m, 3H, H3'+H4'+H5'), 7.90 (m, 2H, H2'+H6'), 12.68 (s, 1H, 5OH); MS (EI) m/z 312 ([M]$^+$, base), 283.

5-Hydroxy-6,7-(dipentyloxy)flavone (40). A mixture of 1 (51 mg, 0.19 mmol), 1-iodopentane (0.076 mL), and anhydrous $K_2CO_3$ (110 mg) in acetone (20 mL) was refluxed with stirring for 24 h. The reaction mixture was concentrated under reduced pressure, diluted with water (40 mL) and extracted with $CH_2Cl_2$ (40 mL×3). The extract was washed with water and dried over $MgSO_4$ and the solvent evaporated in vacuo. The residue was purified by flash chromatography on a column of silica gel and eluted with $CH_2Cl_2$/MeOH (60:1) to give compound 40 (68 mg, 87%) as a pale yellow powder. mp 111-112° C.; $^1H$ NMR ($CDCl_3$) δ 0.94, 0.97 (each t, 6H, H5a, H5b, J=6.6 Hz), 1.39-1.52 (m, 8H, H3a+H4a+H3b+H4b), 1.81, 1.91 (each quintet, 4H, H2a, H2b, J=6.6 Hz), 4.05, 4.09 (each t, 4H, H1a, H1b, J=6.6 Hz), 6.56 (s, 1H, H3), 6.68 (s, 1H, H8), 7.54 (m, 3H, H3'+H4'+H5'), 7.90 (m, 2H, H2'+H6'); MS (EI) m/z 410 [M]$^+$.

5-Methoxy-6,7-(dipentyloxy)flavone (41). To a stirred solution of 40 (33 mg, 0.08 mmol) in a mixture of MeOH (4 mL) and THF (8 mL) was added $TMSCHN_2$ (2M in hexanes, 0.32 mL, 0.64 mmol). The reaction mixture was stirred at room temperature for 24 h and evaporated. Flash chromatography of the residue, eluting with $CH_2Cl_2$/acetone (20:1), gave compound 41 (32.6 mg, 98%) as a white solid. mp 107-108° C.; $^1H$ NMR ($CDCl_3$) δ 0.95, 0.97 (each t, 6H, H5a, H5b, J=6.6 Hz), 1.39-1.54 (m, 8H, H3a+H4a+H3b+H4b), 1.81, 1.93 (each quintet, 4H, H2a, H2b, J=6.6 Hz), 3.99 (s, 3H, H1c), 4.03, 4.10 (each t, 4H, H1a, H1b, J=6.6 Hz), 6.78 (s, 1H, H3), 6.81 (s, 1H, H8), 7.53 (m, 3H, H3'+H4'+H5'), 7.90 (m, 2H, H2'+H6'); MS (EI) m/z 424 [M]$^+$.

6,7-(Dihexyloxy)-5-hydroxyflavone (42). A mixture of 1 (54 mg, 0.2 mmol), 1-bromohexane (0.084 mL), and anhydrous $K_2CO_3$ (110 mg) in acetone (20 mL) was refluxed with stirring for 24 h. The reaction mixture was concentrated under reduced pressure, diluted with water (40 mL) and extracted with $CH_2Cl_2$ (40 mL×3). The extract was washed with water and dried over $MgSO_4$ and the solvent evaporated iit vacuo. The residue was purified by flash chromatography on a column of silica gel and eluted with $CH_2Cl_2$/MeOH (60:1) to give compound 42 (71.4 mg, 82%) as a pale yellow powder. mp 96-97° C.; $^1$H NMR ($CDCl_3$) δ 0.92, 0.93 (each t, 6H, H6a, H6b, J=6.6 Hz), 1.32-1.41 (m, 8H, H4a+H5a+H4b+H5b), 1.48-1.53 (m, 4H, H3a+H3b), 1.80, 1.90 (each quintet, 4H, H2a, H2b, J=6.6 Hz), 4.05, 4.09 (each t, 4H, H1a, H1b, J=6.6 Hz), 6.56 (s, 1H, H3), 6.68 (s, 1H, H8), 7.54 (m, 3H, H3'+H4'+H5'), 7.90 (m, 2H, H2'+H6'); MS (EI) m/z 438 [M]$^+$.

6,7-(Dihexyloxy)-5-methoxyflavone (43). To a stirred solution of 42 (47 mg, 0.1 mmol) in a mixture of MeOH (4 mL) and THF (8 mL) was added $TMSCHN_2$ (2M in hexanes, 0.4 mL, 0.8 mmol). The reaction mixture was stirred at room temperature for 24 h and evaporated. Flash chromatography of the residue, eluting with $CH_2Cl_2$/acetone (15:1), gave compound 43 (41 mg, 91%) as a white solid. mp 93-95° C.; $^1$H NMR ($CDCl_3$) δ 0.92, 0.94 (each t, 6H, H6a, H6b, J=6.6 Hz), 1.30-1.41 (m, 8H, H4a+H5a+H4b+H5b), 1.51-1.55 (m, 4H, H3a+H3b), 1.80, 1.92 (each quintet, 4H, H2a, H2b, J=6.6 Hz), 3.99 (s, 3H, H1c), 4.03, 4.10 (each t, 4H, H1a, H1b, J=6.6 Hz), 6.76 (s, 1H, H3), 6.81 (s, 1H, H8), 7.52 (m, 3H, H3'+H4'+H5'), 7.90 (m, 2H, H2'+H6'); MS (ED) m/z 452 [M]$^+$.

6,7-Diethoxy-5-methoxyflavone (44). To a stirred solution of 33 (33 mg, 0.1 mmol) in a mixture of MeOH (4 mL) and THF (8 mL) was added $TMSCHN_2$ (2M in hexanes, 0.4 mL, 0.8 mmol). The reaction mixture was stirred at room temperature for 24 h and evaporated. Flash chromatography of the residue, eluting with $CH_2Cl_2$/acetone (10:1 to 5:1), afforded compound 44 (33.8 mg, 99%) as a white solid. mp 126-128° C.; $^1$H NMR ($CDCl_3$) δ 1.42, 1.55 (each t, 6H, H2a, H2b, J=6.9 Hz), 4.00 (s, 3H, H1c), 4.13, 4.19 (each q, 4H, H1a, H1b, J=6.9 Hz), 6.77 (s, 1H, H3), 6.81 (s, 1H, H8), 7.52 (m, 3H, H3'+H4'+H5'), 7.90 (m, 2H, H2'+H6'); MS (EI) m/z 340 [M]$^+$.

6,7-Dibutoxy-5-hydroxyflavone (45). A mixture of 1 (81 mg, 0.3 mmol), 1-iodobutane (0.1 mL), and anhydrous $K_2CO_3$ (165 mg) in acetone (20 mL) was refluxed with stirring for 24 h. The reaction mixture was concentrated under reduced pressure, diluted with water (50 mL) and extracted with $CH_2Cl_2$ (3×50 mL). The extract was washed with water and dried over $MgSO_4$, and the solvent was evaporated in vacuo. The residue was purified by flash chromatography on a column of silica gel eluted with $CH_2Cl_2$/MeOH (60:1) to give compound 45 (86 mg, 75%) as a yellow powder. mp 116-117° C.; $^1$H NMR ($CDCl_3$) δ 0.99, 1.02 (each t, 6H, H4a, H4b, J=6.6 Hz), 1.53-1.58 (m, 4H, H3a+H3b), 1.79, 1.89 (each quintet, 4H, H2a, H2b, J=6.6 Hz), 4.06, 4.10 (each t, 4H, H1a, H1b, J=6.6 Hz), 6.56 (s, 1H, H3), 6.68 (s, 1H, H8), 7.54 (m, 3H, H3'+H4'+H5'), 7.90 (m, 2H, H2'+H6'); MS (EI) m/z 382 [M]$^+$.

6,7-Dibutoxy-5-methoxyflavone (46). To a stirred solution of 45 (49 mg, 0.128 mmol) in a mixture of MeOH (5 mL) and THF (10 mL) was added $TMSCHN_2$ (2M in hexanes, 0.5 mL, 1 mmol). The reaction mixture was stirred at room temperature for 24 h, and then evaporated. Flash chromatography of the residue, eluting with $CH_2Cl_2$/acetone (15:1), gave compound 46 (46 mg, 91%) as a white solid. mp 103-105° C.; $^1$H NMR ($CDCl_3$) δ 0.99, 1.03 (each t, 6H, H4a, H4b, J=6.6 Hz), 1.55-1.59 (m, 4H, H3a+H3b), 1.78, 1.91 (each quintet, 4H, H2a, H2b, J=6.6 Hz), 3.99 (s, 3H, H1c), 4.04, 4.11 (each t, 4H, H1a, H1b, J=6.6 Hz), 6.81 (s, 1H, H3), 6.82 (s, 1H, H8), 7.53 (m, 3H, H3'+H4'+H5'), 7.90 (m, 2H, H2'+H6'); MS (EI) m/z 396 [M]$^+$.

Biological Experiments

Vinblastine uptake by the KB/MDR cells. KB/MDR cells,[37] which overexpress human P-gp 170 protein, were seeded into 24-well tissue culture plates in RPMI 1640 medium plus 10% fetal bovine serum for 24 hours without the selecting agent doxorubicin (37 nM). The cells were then treated with [$^3$H]vinblastine plus synthetic flavones in HBSS for 60 minutes. The cells were washed twice with ice-cold PBS, harvested with 1 N NaOH, neutralized with 1 N HCl. The cell aliquots were transferred to scintillation vials and counted with a γ-counter (Beckman, model LS 5000) after adding 10 mL scintillation fluids (SafeScint, American Bioanalytical Co., Natick, Mass.). Data presented are the mean of three independent experiments.

Growth Inhibitory Assay: Approximately $10^4$ KB or KB/MDR cells were seeded into 24-well tissue culture plates in RPMI 1640 medium plus 10% fetal bovine serum for 24 hours, after which the cells were treated with various concentrations of synthetic flavones in culture medium for 3 days. The cells were then fixed and stained with methylene blue in 50% MeOH, washed thoroughly with tap water, and dissolved with 0.5 mL 0.5% sarcosyl.[38] The amount of cellular protein, which is proportional to the cell number, is estimated by the absorption ($OD_{595nm}$). The growth inhibitory assay, which is presented as an $IC_{50}$ value, represents the concentration of compound required to inhibit 50% of cell growth. The cell doubling time of KB and KB/MDR cells is about 20 to 24 hours. The data presented are the mean of three independent experiments.

It is to be understood by those skilled in the art that the foregoing description and examples are illustrative of practicing the present invention, but are in no way limiting. Variations of the detail presented herein may be made without departing from the spirit and scope of the present invention as defined by the following claims.

REFERENCES (1) Germann, U. A. P-glycoprotein--a mediator of multidrug resistance in tumour cells. *Eur J Cancer* 1996, 32A, 927-944.

(2) Gottesman, M. M.; Pastan, I. Biochemistry of multidrug resistance mediated by the multidrug transporter. *Annu Rev Biochem* 1993, 62, 385-427.

(3) Thiebaut, F.; Tsuruo, T.; Hamada, H.; Gottesman, M. M.; Pastan, I. et al. Cellular localization of the multidrug-resistance gene product P-glycoprotein in normal human tissues. *Proc Natl Acad Sci USA* 1987, 84, 7735-7738.

(4) Borst, P.; Schinkel, A. H. What have we learnt thus far from mice with disrupted P-glycoprotein genes? *Eur J Cancer* 1996, 32A, 985-990.

(5) Luker, G. D.; Nilsson, K. R.; Covey, D. F.; Piwnica-Worms, D. Multidrug resistance (MDR1) P-glycoprotein enhances esterification of plasma membrane cholesterol. *J Biol Chem* 1999, 274, 6979-6991.

(6) Dalton, W. S.; Grogan, T. M.; Meltzer, P. S.; Scheper, R. J.; Durie, B. G. et al. Drug-resistance in multiple myeloma and non-Hodgkin's lymphoma: detection of P-glycoprotein and potential circumvention by addition of verapamil to chemotherapy. *J Clin Oncol* 1989, 7, 415-424.

(7) Miller, T. P.; Grogan, T. M.; Dalton, W. S.; Spier, C. M.; Scheper, R. J. et al. P-glycoprotein expression in malignant lymphoma and reversal of clinical drug resistance with chemotherapy plus high-dose verapamil. *J Clin Oncol* 1991, 9, 17-24.

(8) Nuessler, V.; Scheulen, M. E.; Oberneder, R.; Kriegmair, M.; Goebel, K. J. et al. Phase I and pharmacokinetic study of the P-glycoprotein modulator dexniguldipine-HCL. *Eur J Med Res* 1997, 2, 55-61.

(9) Wilson, W. H.; Jamis-Dow, C.; Bryant, G.; Balis, F. M.; Klecker, R. W. et al. Phase I and pharmacokinetic study of the multidrug resistance modulator dexverapamil with EPOCH chemotherapy. *J Clin Oncol* 1995, 13, 1985-1994.

(10) Hyafil, F.; Vergely, C.; Du Vignaud, P.; Grand-Perret, T. In vitro and in vivo reversal of multidrug resistance by GF120918, an acridonecarboxamide derivative. *Cancer Res* 1993, 53, 4595-4602.

(11) Boesch, D.; Gaveriaux, C.; Jachez, B.; Pourtier-Manzanedo, A.; Bollinger, P. et al. In vivo circumvention of P-glycoprotein-mediated multidrug resistance of tumor cells with SDZ PSC 833. *Cancer Res* 1991, 51, 4226-4233.

(12) Ramu, A.; Spanier, R.; Rahamimoff, H.; Fuks, Z. Restoration of doxorubicin responsiveness in doxorubicin-resistant P388 murine leukaemia cells. *Br J Cancer* 1984, 50, 501-507.

(13) Middleton, E., Jr.; Kandaswami, C.; Theoharides, T. C. The effects of plant flavonoids on mammalian cells: implications for inflammation, heart disease, and cancer *Pharmacol Rev* 2000, 52, 673-751.

(14) Bailey, D. G.; Malcolm, J.; Arnold, O.; Spence, J. D. Grapefruit juice-drug interactions. *Br J Clin Pharmacol* 1998, 46, 101-110.

(15) Ducharme, M. P.; Warbasse, L. H.; Edwards, D. J. Disposition of intravenous and oral cyclosporine after administration with grapefruit juice. *Clin Pharmacol Ther* 1995, 57, 485-491.

(16) De Vincenzo, R.; Scambia, G; Benedetti Panici, P.; Ranelletti, F. O.; Bonanno, G et al. Effect of synthetic and naturally occurring chalcones on ovarian cancer cell growth: structure-activity relationships. *Anticancer Drug Des* 1995, 10, 481-490.

(17) Murakami, S.; Muramatsu, M.; Tomisawa, K. Inhibition of gastric H+, K(+)-ATPase by flavonoids: a structure-activity study. *J Enzymne Inhib* 1999, 14, 151-166.

(18) Akiyama, T.; Ishida, J.; Nakagawa, S.; Ogawara, H.; Watanabe, S. et al. Genistein, a specific inhibitor of tyrosine-specific protein kinases. *J Biol Chem* 1987, 262, 5592-5595.

(19) De Azevedo, W. F., Jr.; Mueller-Dieckmann, H. J.; Schulze-Gahmen, U.; Worland, P. J.; Sausville, E. et al. Structural basis for specificity and potency of a flavonoid inhibitor of human CDK2, a cell cycle kinase. *Proc Natl Acad Sci USA* 1996, 93, 2735-2740.

(20) Boumendjel, A.; Di Pietro, A.; Dumontet, C.; Barron, D. Recent advances in the discovery of flavonoids and analogs with high-affinity binding to P-glycoprotein responsible for cancer cell multidrug resistance. *Med Res Rev* 2002, 22, 512-529.

(21) Conseil, G.; Baubichon-Cortay, H.; Dayan, G; Jault, J. M.; Barron, D. et al. Flavonoids: a class of modulators with bifunctional interactions at vicinal ATP- and steroid-binding sites on mouse P-glycoprotein. *Proc Natl Acad Sci USA* 1998, 95, 9831-9836.

(22) Perez-Victoria, J. M.; Perez-Victoria, F. J.; Conseil, G; Maitrejean, M.; Comte, G et al. High-affinity binding of silybin derivatives to the nucleotide-binding domain of a Leishmania tropica P-glycoprotein-like transporter and chemosensitization of a multidrug-resistant parasite to daunomycin. *Antimicrob Agents Chemother* 2001, 45, 439-446.

(23) Thiyagarajah, P.; Kuttan, S. C.; Lim, S. C.; Teo, T. S.; Das, N. P. Effect of myricetin and other flavonoids on the liver plasma membrane Ca2+ pump. Kinetics and structure-function relationships. *Biochenm Pharmacol* 1991, 41, 669-675.

(24) Hirano, T.; Oka, K.; Akiba, M. Effects of synthetic and naturally occurring flavonoids on Na+,K+-ATPase: aspects of the structure-activity relationship and action mechanism. *Life Sci* 1989, 45, 1111-1117.

(25) Jinsart, W.; Ternai, B.; Polya, G M. Inhibition of rat liver cyclic AMP-dependent protein kinase by flavonoids. *Biol Chem Hoppe Seyler* 1992, 373, 205-211.

(26) Ferriola, P. C.; Cody, V.; Middleton, E., Jr. Protein kinase C inhibition by plant flavonoids. Kinetic mechanisms and structure-activity relationships. *Bioclem Pharmacol* 1989, 38, 1617-1624.

(27) Hagiwara, M.; Inoue, S.; Tanaka, T.; Nunoki, K.; Ito, M. et al. Differential effects of flavonoids as inhibitors of tyrosine protein kinases and serine/threonine protein kinases. *Biochem Pharmacol* 1988, 37, 2987-2992.

(28) Perez-Victoria, J. M.; Chiquero, M. J.; Conseil, G.; Dayan, G.; Di Pietro, A. et al. Correlation between the affinity of flavonoids binding to the cytosolic site of Leishmania tropica multidrug transporter and their efficiency to revert parasite resistance to daunomycin. *Biocheimistry* 1999, 38, 1736-1743.

(29) Lo, A.; Burckart, G. J. P-glycoprotein and drug therapy in organ transplantation. *J Clin Pharmacol* 1999, 39, 995-1005.

(30) Wang, R. B.; Kuo, C. L.; Lien, L. L.; Lien, E. J. Structure-activity relationship: analyses of p-glycoprotein substrates and inhibitors. *J Clin Pharm Ther* 2003, 28, 203-228.

(31) Di Pietro, A.; Conseil, G.; Perez-Victoria, J. M.; Dayan, G.; Baubichon-Cortay, H. et al. Modulation by flavonoids of cell multidrug resistance mediated by P-glycoprotein and related ABC transporters. *Cell Mol Life Sci* 2002, 59, 307-322.

(32) Chambers, T. C.; Pohl, J.; Raynor, R. L.; Kuo, J. F. Identification of specific sites in human P-glycoprotein phosphorylated by protein kinase C. *J Biol Chem;* 1993, 268, 4592-4595.

(33) Callaghan, R.; Higgins, C. F. Interaction of tamoxifen with the multidrug resistance P-glycoprotein. *Br J Cancer* 1995, 71, 294-299.

(34) Smith, C. D.; Zilfou, J. T. Circumvention of P-glycoprotein-mediated multiple drug resistance by phosphorylation modulators is independent of protein kinases. *J Biol Chem* 1995, 270, 28145-28152.

(35) Conseil, G; Perez-Victoria, J. M.; Jault, J. M.; Gamarro, F.; Goffeau, A. et al. Protein kinase C effectors bind to multidrug ABC transporters and inhibit their activity. *Biochenmistry* 2001, 40, 2564-2571.

(36) Dayan, G.; Jault, J. M.; Baubichon-Cortay, H.; Baggetto, L. G.; Renoir, J. M. et al. Binding of steroid modulators to recombinant cytosolic domain from mouse P-glycoprotein in close proximity to the ATP site. *Biochemistry* 1997, 36, 15208-15215.

(37) Chen, H. X.; Bamberger, U.; Heckel, A.; Guo, X.; Cheng, Y. C. BIBW 22, a dipyridamole analogue, acts as a bifunctional modulator on tumor cells by influencing both P-glycoprotein and nucleoside transport. *Cancer Res* 1993, 53, 1974-1977.

The invention claimed is:

1. A method of facilitating or enhancing the bioavailability of a bioactive agent or drug, the activity of which is diminished by P-gp170 or CYP450 in a patient or subject, said method comprising co-administering with said bioactive agent or drug to said patient or subject an effective amount of at least one bioavailability enhancing agent according to the formula:

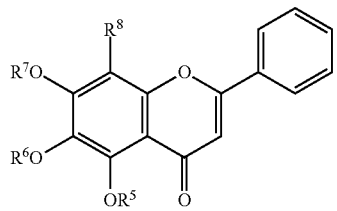

where $R^5$ is an optionally substituted phenyl or benzyl group, an acyl group, a $C_1$-$C_{20}$ alkyl or ether group, a phosphate, diphosphate, triphosphate or phosphodiester group;

$R^6$ and $R^7$ are each independently H, ($C_1$-$C_{12}$)alkyl, ($C_2$-$C_{13}$)acyl, or an optionally substituted phenyl or benzyl or together with the oxygen atoms to which they are attached form a —OCR$^1$R$^2$O— group wherein each of $R^1$ and $R^2$ is independently H, a $C_1$-$C_3$ alkyl group or an optionally substituted phenyl or benzyl group; and $R^8$ is H, OH, an O-acyl group, a $C_1$-$C_4$ alkyl or alkoxy group, F, Cl, Br or I; or a pharmaceutically acceptable salt thereof.

2. The method according to claim 1 wherein said bioactive agent is an anti-cancer agent.

3. The method according to claim 2 wherein said anticancer agent is selected from the group consisting of Ara C, etoposide, doxorubicin, daunorubicin, mitoxantrone, idarubicin, vinblastine, vincristine, taxol, hydroxyurea, colchicine, etoposide, tenoposide, actinomycin D, puromycin, valinomycin, mithramycin, gramicidin D, emetine, rhodamine 123, cytoxan, DiOC2, Hoechst 33342, mitomycin C, adriamycin, topotecan, campothecin, irinotecan, gemcitabine, cisplatin and mixtures thereof.

4. The method according to claim 1 wherein $R^5$ is a methyl, acetyl or benzyl group, $R^6$ and $R^7$ is each independently a $C_1$-$C_8$ alkyl group, an acetyl or benzyl group, or $R^6$ and $R^7$ together form a $CH_2$ group or a $CPh_2$ group; and $R^8$ is H or Br.

5. The method according to claim 1 wherein $R^8$ is Br.

6. The method according to claim 1 wherein $R^8$ is H or Br.

7. The method according to claim 1 wherein $R^8$ is H.

8. The method of claim 1 wherein said bioactive agent or drug acts on the central nervous system.

9. The method of claim 1 wherein said bioactive agent acts on the brain.

10. The method of claim 1 wherein said bioactive agent attains a level which is at least twice the level attained in the absence of said enhancing agent.

11. The method according to claim 1 wherein said bioactive agent is an antitumor or anticancer agent.

12. The method according to claim 1 wherein said bioactive agent or drug is selected from the group consisting of anesthetics, systemic antibiotics, antiparasitics, systemic quinolones, anti-infectives, anti-inflammatories, aminoglycosides, cephalosporins, penicillins, antidotes, anti-cholinesterases, metal poisoning antidotes, anticancer agents, cytotoxic agents, hormones, steroids, immunomodulators, cytokines, systemic antivirals, systemic antifungals, biologicals, alpha-antitrypsin, bone metabolism regulators, hypercalcemic agent, cardiovascular agents, beta blockers, cerebral vasodilators, cerebral metabolic enhancers, cholinesterase inhibitors, vasopressors, local diabetic agents, diagnostics, adenosine deaminase deficiency agents, gonadotropin inhibitors, adrenal cortical steroid inhibitors, gonadotropin releasing hormone stimulant, urofollitropins, muscle relaxants such as neuromuscular blocking agents, prostaglandin analogs, prostaglandins, prostaglandin inhibitors, respiratory therapy agents, anticholinergics, beta andrenergic stimulators, sympathomimetics, and thrombolytics, antithrobotics, anticoagulants, antibiotics antiplatelet agents, thrombolytics, antiproliferatives, steroidal and nonsteroidal antiinflammatories, agents that inhibit hyperplasia, smooth muscle cell inhibitors, growth factors, growth factor inhibitors, cell adhesion inhibitors, cell adhesion promoters, endothelial cell regeneration agents, antiinflammatory drugs, antibacterials, antiprotazoals, antifungals, coronary vasodilators, calcium channel blockers, bronchodilators, enzyme inhibitors, antihypertensives, anti-ulceratives, steroidal hormones, antivirals, immunomodulators, local anesthetics, cardiotonics, antitussives, antihistamines, narcotic analgesics, peptide hormones, cardioactive products, enzymes, antinauseants, anticonvulsants, immunosuppressives, psychotherapeutics, sedatives, hypnotics, anticoagulants, analgesics, antimigraine agents, antiarrhythmic agents, antiemetics, neurologic agents, hemostatics, anti-obesity agents, antigout agents, antianxiety agents, immunosuppressive agents, hyperlipidemic agents, antiparkinson agents, antifungal agents, antimanic agents, antipyretics, antiarthritic agents, antiplatetet agents, anticonvulsants, antidiabetic agents, anticoagulants, antiarrhythmics, antianginal agents, or mixtures thereof.

13. A method of facilitating or enhancing the bioavailability of a bioactive agent or drug, the activity of which is diminished by P-gp170 or CYP450 in a patient or subject, said method comprising co-administering with said bioactive agent or drug to said patient or subject an effective amount of at least one bioavailability enhancing agent according to the formula:

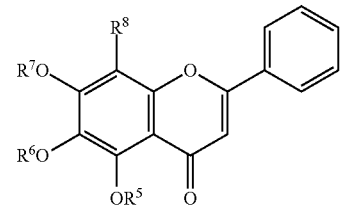

where $R^5$ is a benzyl group (Bn), $R^6$ is an acetyl group (Ac); $R^7$ is an acetyl group (Ac) and $R^8$ is H; or
$R^5$ is H, $R^6$ is Bn; $R^7$ is Ac and $R^8$ is H; or
$R^5$ is Ac, $R^6$ is Ac; $R^7$ is Bn and $R^8$ is H;
$R^5$ is H, $R^6$ is Bn $R^7$ is H and $R^8$ is H;
$R^5$ is H, $R^6$ is Bn; $R^7$ is Bn and $R^8$ is H;
$R^5$ is a methyl group (Me), $R^6$ and $R^7$ together form a $CPh_2$ group and $R^8$ is H;
$R^5$ is H, $R^6$ is Ac; $R^7$ is H and $R^8$ is H;
$R^5$ is H, $R^6$ is Ac; $R^7$ is Ac and $R^8$ is H;
$R^5$ is Ac, $R^6$ is Ac; $R^7$ is Ac and $R^8$ is H;
$R^5$ is Me, $R^6$ is Ac; $R^7$ is Ac and $R^8$ is H.;
$R^5$ is Me, $R^6$ is Ac; $R^7$ is Me and $R^8$ is H;
$R^5$ is H, $R^6$ is Ac; $R^7$ is Ac and $R^8$ is Br;
$R^5$ is H, $R^6$ is H; $R^7$ is H and $R^8$ is Br;
$R^5$ is H, $R^6$ is Me; $R^7$ is Me and $R^8$ is .H;

$R^5$ is Me, $R^6$ is Me; $R^7$ is Me and $R^8$ is H;
$R^5$ is H, $R^6$ and $R^7$ together with the oxygen atoms to which they are attached form a $OCH_2$ group and $R^8$ is H;
$R^5$ is Me, $R^6$ and $R^7$ together with the oxygen atoms to which they are attached form a $OCH_2O$ group and $R^8$ is H;
$R^5$ is H, $R^6$ is ethyl (Et); $R^7$ is H and $R^8$ is H;
$R^5$ is H, $R^6$ is Et; $R^7$ is Me and $R^8$ is H; or
$R^5$ H, $R^6$ is Et; $R^7$ is Et and $R^8$ is H;
$R^5$ Me, $R^6$ is Et; $R^7$ is Et and $R^8$ is H;
$R^5$ H, $R^6$ is propyl (Pr); $R^7$ is H and $R^8$ is H;
$R^5$ H, $R^6$ is Pr; $R^7$ is Me and $R^8$ is H;
$R^5$ Me, $R^6$ is Pr; $R^7$ is Me and $R^8$ is H;
$R^5$ H, $R^6$ is Pr; $R^7$ is Pr and $R^8$ is H;
$R^5$ Me $R^6$ is Pr; $R^7$ is Pr and $R^8$ is H;
$R^5$ H, $R^6$ is $C_4H_9$; $R^7$ is $C_4H_9$ and $R^8$ is H;
$R^5$ Me, $R^6$ is $C_4H_9$; $R^7$ is $C_4H_9$ and $R^8$ is H;
$R^5$ H, $R^6$ is $C_5H_{11}$; $R^7$ is $C_5H_{11}$ and $R^8$ is H;
$R^5$ Me, $R^6$ is $C_5H_{11}$; $R^7$ is $C_5H_{11}$ and $R^8$ is H;
$R^5$ H, $R^6$ is $C_6H_{13}$; $R^7$ is $C_6H_{13}$ and $R^8$ is H;
$R^5$ Me, $R^6$ is $C_6H_{13}$; $R^7$ is $C_6H_{13}$ and $R^8$ is H; or
$R^5$ H, $R^6$ is $C_8H_{17}$; $R^7$ is $C_8H_{17}$ and $R^8$ is H; or
a pharmaceutically acceptable salt thereof.

14. The method of claim 13 wherein said bioactive agent or drug acts on the central nervous system.

15. The method of claim 13 wherein said bioactive agent acts on the brain.

16. The method of claim 13 wherein said bioactive agent attains a level which is at least twice the level attained in the absence of said enhancing agent.

17. The method according to claim 13 wherein said bioactive agent is an antitumor or anticancer agent.

18. The method according to claim 13 wherein said bioactive agent is an anti-cancer agent.

19. The method according to claim 13 wherein said anticancer agent is selected from the group consisting of Ara C, etoposide, doxorubicin, daunorubicin, mitoxantrone, idarubicin, vinblastine, vincristine, taxol, hydroxyurea, colchicine, etoposide, tenoposide, actinomycin D, puromycin, valinomycin, mithramycin, gramicidin D, emetine, rhodamine 123, cytoxan, DiOC2, Hoechst 33342, mitomycin C, adriamycin, topotecan, campothecin, irinotecan, gemcitabine, cisplatin and mixtures thereof.

20. The method according to claim 13 wherein said bioactive agent or drug is selected from the group consisting of anesthetics, systemic antibiotics, antiparasitics, systemic quinolones, anti-infectives, anti-inflammatories, aminoglycosides, cephalosporins, penicillins, antidotes, anti-cholinesterases, metal poisoning antidotes, anticancer agents, cytotoxic agents, hormones, steroids, immunomodulators, cytokines, systemic antivirals, systemic antifungals, biologicals, alpha-antitrypsin, bone metabolism regulators, hypercalcemic agent, cardiovascular agents, beta blockers, cerebral vasodilators, cerebral metabolic enhancers, cholinesterase inhibitors, vasopressors, local diabetic agents, diagnostics, adenosine deaminase deficiency agents, gonadotropin inhibitors, adrenal cortical steroid inhibitors, gonadotropin releasing hormone stimulant, urofollitropins, muscle relaxants such as neuromuscular blocking agents, prostaglandin analogs, prostaglandins, prostaglandin inhibitors, respiratory therapy agents, anticholinergics, beta andrenergic stimulators, sympathomimetics, and thrombolytics, antithrobotics, anticoagulants, antibiotics antiplatelet agents, thrombolytics, antiproliferatives, steroidal and nonsteroidal antiinflammatories, agents that inhibit hyperplasia, smooth muscle cell inhibitors, growth factors, growth factor inhibitors, cell adhesion inhibitors, cell adhesion promoters, endothelial cell regeneration agents, antiinflammatory drugs, antibacterials, antiprotazoals, antifungals, coronary vasodilators, calcium channel blockers, bronchodilators, enzyme inhibitors, antihypertensives, anti-ulceratives, steroidal hormones, antivirals, immunomodulators, local anesthetics, cardiotonics, antitussives, antihistamines, narcotic analgesics, peptide hormones, cardioactive products, enzymes, antinauseants, anticonvulsants, immunosuppressives, psychotherapeutics, sedatives, hypnotics, anticoagulants, analgesics, antimigraine agents, antiarrhythmic agents, antiemetics, neurologic agents, hemostatics, anti-obesity agents, antigout agents, antianxiety agents, immunosuppressive agents, hyperlipidemic agents, antiparkinson agents, antifungal agents, antimanic agents, antipyretics, antiarthritic agents, antiplatetet agents, anticonvulsants, antidiabetic agents, anticoagulants, antiarrhythmics, antianginal agents, or mixtures thereof.

21. The method according to claim 13 wherein
$R^5$ is a benzyl group (Bn), $R^6$ is an acetyl group (Ac); $R^7$ is an acetyl group (Ac) and $R^8$ is H; or
$R^5$ is H, $R^6$ is Bn; $R^7$ is Ac and $R^8$ is H; or
$R^5$ is Ac, $R^6$ is Ac; $R^7$ is Bn and $R^8$ is H;
$R^5$ is H, $R^6$ is Bn $R^7$ is H and $R^8$ is H;
$R^5$ is H, $R^6$ is Bn; $R^7$ is Bn and $R^8$ is H;
$R^5$ is a methyl group (Me), $R^6$ and $R^7$ together form a $CPh_2$ group and $R^8$ is H; or
$R^5$ is Me, $R^6$ is Pr, $R^7$ is Pr and $R^8$ is H.

22. The method according to claim 13 wherein
$R^5$ is H, $R^6$ is Ac; $R^7$ is H and $R^8$ is H;
$R^5$ is H, $R^6$ is Ac; $R^7$ is Ac and $R^8$ is H;
$R^5$ is Ac, $R^6$ is Ac; $R^7$ is Ac and $R^8$ is H;
$R^5$ is Me, $R^6$ is Ac; $R^7$ is Ac and $R^8$ is H;
$R^5$ is Me, $R^6$ is Ac; $R^7$ is Me and $R^8$ is H;
$R^5$ is H, $R^6$ is Ac; $R^7$ is Ac and $R^8$ is Br;
$R^5$ is H, $R^6$ is H; $R^7$ is H and $R^8$ is Br; or
$R^5$ is Me, $R^6$ is Pr; $R^7$ is Pr and $R^8$ is H.

23. The method according to claim 13 wherein
$R^5$ is H, $R^6$ is Me; $R^7$ is Me and $R^8$ is H;
$R^5$ is Me, $R^6$; $R^7$ is Me and $R^8$ is H;
$R^5$ is H, $R^6$ and $R^7$ together with the oxygen atoms to which they are attached form a $OCH_2O$ group and $R^8$ is H;
$R^5$ is Me, $R^6$ and $R^7$ together with the oxygen atoms to which they are attached form a $OCH_2O$ group and $R^8$ is H;
$R^5$ is H, $R^6$ is ethyl (Et); $R^7$ is H and $R^8$ is H;
$R^5$ is H, $R^6$ is Et; $R^7$ is Me and $R^8$ is H; or
$R^5$ is Me, $R^6$ is Pr; $R^7$ is Pr and $R^8$ is H.

24. The method according to claim 13 wherein
$R^5$ H, $R^6$ is Et; $R^7$ is Et and $R^8$ is H;
$R^5$ Me, $R^6$ is Et; $R^7$ is Et and $R^8$ is H;
$R^5$ H, $R^6$ is propyl (Pr); $R^7$ is H and $R^8$ is H;
$R^5$ H, $R^6$ is Pr; $R^7$ is Me and $R^8$ is H;
$R^5$ Me, $R^6$ is Pr; $R^7$ is Me and $R^8$ is H;
$R^5$ H, $R^6$ is Pr; $R^7$ is Pr and $R^8$ is H;
$R^5$ Me, $R^6$ is Pr; $R^7$ is Pr and $R^8$ is H;
$R^5$ H, $R^6$ is $C_4H_9$; $R^7$ is $C_4H_9$ and $R^8$ is H;
$R^5$ Me, $R^6$ is $C_4H_9$; $R^7$ is $C_4H_9$ and $R^8$ is H;
$R^5$ H, $R^6$ is $C_5H_{11}$; $R^7$ is $C_5H_{11}$ and $R^8$ is H;
$R^5$ Me, $R^6$ is $C_5H_{11}$; $R^7$ is $C_5H_{11}$ and $R^8$ is H;
$R^5$ H, $R^6$ is $C_6H_{13}$; $R^7$ is $C_6H_{13}$ and $R^8$ is H;
$R^5$ Me, $R^6$ is $C_6H_{13}$; $R^7$ is $C_6H_{13}$ and $R^8$ is H; or
$R^5$ H, $R^6$ is $C_8H_{17}$; $R^7$ is $C_8H_{17}$ and $R^8$ is H or
$R^5$ is Me, $R^6$ is Pr; $R^7$ is Pr and $R^8$ is H.

* * * * *